(12) United States Patent
Bailey

(10) Patent No.: US 11,123,349 B2
(45) Date of Patent: Sep. 21, 2021

(54) METHOD OF TREATMENT

(71) Applicant: The University of Melbourne, Melbourne (AU)

(72) Inventor: Simon R. Bailey, Melbourne (AU)

(73) Assignee: THE UNIVERSITY OF MELBOURNE, Victoria (AU)

( * ) Notice: Subject to any disclaimer, the term of this patent is extended or adjusted under 35 U.S.C. 154(b) by 0 days.

(21) Appl. No.: 16/485,874

(22) PCT Filed: Feb. 15, 2018

(86) PCT No.: PCT/AU2018/050120
§ 371 (c)(1),
(2) Date: Aug. 14, 2019

(87) PCT Pub. No.: WO2018/148797
PCT Pub. Date: Aug. 23, 2018

(65) Prior Publication Data
US 2020/0061074 A1    Feb. 27, 2020

(30) Foreign Application Priority Data

Feb. 15, 2017 (AU) ............... 2017900491

(51) Int. Cl.
| A61K 31/5377 | (2006.01) |
| A61P 37/02 | (2006.01) |
| A61K 9/00 | (2006.01) |
| A61K 47/40 | (2006.01) |

(52) U.S. Cl.
CPC ........ *A61K 31/5377* (2013.01); *A61K 9/0019* (2013.01); *A61K 47/40* (2013.01); *A61P 37/02* (2018.01)

(58) Field of Classification Search
CPC ............................ A61K 31/5377; A61P 37/02
See application file for complete search history.

(56) References Cited

U.S. PATENT DOCUMENTS 6,319,921 B1 * 11/2001 Cirillo ................. C07D 405/12
514/236.5
2003/0068340 A1    4/2003 Cappola et al.

FOREIGN PATENT DOCUMENTS

| WO | 00/43384 A1 | 7/2000 |
| WO | 2005/060967 A1 | 7/2005 |

OTHER PUBLICATIONS

Sykes et al., "Equine endotoxemia—A state-of-the-art review of therapy", Australian Veterinary Journal, vol. 83, No. 1-2, pp. 45-50 (2005).*
Neuder, et al., "Role of p38 MAPK in LPS induced pro-inflammatory cytokine and chemokine gene expression in equine leukocytes", Veterinary Immunology Immunopathology, vol. 129(3-4), pp. 192-199, Jun. 15, 2009.
Eckert, et al., "The role of p38 mitogen-activated kinase (MAPK) in the mechanism regulating cyclooxygenase gene expression in equine leukocytes", Veterinary Immunology Immunopathology, vol. 118 (3-4), pp. 294-303, Aug. 15, 2007.
Brooks, et al., "Regulation of platelet activating factor-induced equine platelet activation by intracellular kinases", The Journal of Veterinary Pharmacology and Therapeutics, vol. 32(2), pp. 189-196, Apr. 2009.
De Jonge, et al., "P38 MAPK Inhibitor Semapimod Reduces Postoperative Ileus Via Peripheral and Central Mechanisms", Gastroenterology, vol. 136, Issue 5, pp. 1841-1842, May 2009.
Xing, et al., "Clinical candidates of small molecule p38 MAPK inhibitors for inflammatory diseases", MAP Kinase, vol. 4, No. 1, pp. 24-30, 2015.
Moore, "Recognition and treatment of endotoxemia", Veterinary Clinics of North America: Equine Practice, vol. 4(1), pp. 105-113, Apr. 1988.
van Deventer, et al., "Intestinal Endotoxemia", Gastroenterology, vol. 94, pp. 825-831, 1988.
Woolcock, "Pathogenesis of bacterial infections: some determinants of virulence in Gram negative bacteria", Australian Veterinary Journal, vol. 62(6), pp. 177-181, Jun. 1985.
McCue, "Improved Mortality in Gram-negative Bacillary Bacteremia", Archives of Internal Medicine, vol. 145(7), pp. 1212-1216, Jul. 1985.
Balis, et al., "Glucocorticoid and antibiotic effects on hepatic microcirculation and associated host responses in lethal gram-negative bacteremia", Laboratory Investigation, vol. 40(1), pp. 55-65, Jan. 1979.
Morris, "Endotoxemia in horses. A review of cellular and humoral mediators involved in its pathogenesis", Journal of Veterinary Internal Medicine, vol. 5(3), pp. 167-181, May-Jun. 1991.
Moore, et al., "Is it the systemic inflammatory response syndrome or endotoxemia in horses with colic?", Veterinary Clinics of North America: Equine Practice, vol. 30(2), pp. 337-351, Aug. 2014.
Fehr, et al., "Impact of p38 MAP Kinase Inhibitors on LPS-Induced Release of TNF-α in Whole Blood and Primary Cells from Different Species", Cellular Physiology & Biochemistry, vol. 36(6), pp. 2237-2249, 2015.

(Continued)

*Primary Examiner* — Kevin E Weddington
(74) *Attorney, Agent, or Firm* — BakerHostetler

(57) ABSTRACT

The present invention relates to the treatment of equine animals presenting with an inflammatory condition and/or symptoms associated with inflammation and/or which have a condition which could lead to an inflammatory disorder. Formulations and therapeutic protocols useful for the treatment of inflammation and amelioration of symptoms associated with inflammation also form part of the present invention.

17 Claims, 19 Drawing Sheets

(56) References Cited

OTHER PUBLICATIONS

Breuer, et al., "Establishing a sepsis-score for adult equine patients", Pferdeheilkunde, vol. 28(4), pp. 421-428, Jul. 2012.
Balk, "Systemic inflammatory response syndrome (SIRS)", Virulence, 5(1), pp. 20-26, Jan. 1, 2014.
Shenep, et al., "Serial quantitation of endotoxemia and bacteremia during therapy for gram-negative bacterial sepsis", Journal of Infectious Diseases, vol. 157(3), pp. 565-568, Mar. 1988.
Morris, "Endotoxemia in horses. A review of cellular and humoral mediators involved in its pathogenesis", J Vet Intern Med, vol. 5, No. 3, pp. 167-181, 1991.

* cited by examiner

METHOD OF TREATMENT

CROSS-REFERENCE TO RELATED APPLICATIONS

This application is the National Stage Application of International Patent Application No. PCT/AU2018/050120, filed Feb. 15, 2018, which is associated with and claims priority from Australian Provisional Patent Application No. 2017900491, filed on Feb. 15, 2017, entitled "A method of treatment", the entire contents of each of which are incorporated herein by reference in their entirety.

FIELD

The present invention relates to the treatment of equine animals presenting with an inflammatory condition and/or symptoms associated with inflammation and/or which have a condition which could lead to an inflammatory disorder. Formulations and therapeutic protocols useful for the treatment of inflammation and amelioration of symptoms associated with inflammation also form part of the present invention.

BACKGROUND

Bibliographic details of the publications referred to by author in this specification are collected alphabetically at the end of the description.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavor to which this specification relates.

Inflammatory conditions in horses are complex, multifaceted disorders with mixed etilogies. Endotoxemia, for example, is a condition which contributes to significant levels of risk of morbidity and mortality in horses. It is a condition characterized by infiltration of Gram-negative bacteria and their endotoxins into the horse's circulatory system. This results in bacterial septicaemia (bacteremia) and systemic inflammation. An endotoxin is a structural component of the outer cell membrane of Gram-negative bacteria and comprises lipid A linked via a core oligosaccharide to a polysaccharide. The latter polysaccharide confers serologic specificity to the endotoxin. It is often referred to as a lipopolysaccharide (LPS). As LPS is a significant component of the outer cell wall of the bacterium, it is liberated upon death and lysis of the bacterium or when the bacterium undergoes rapid division (Moore (1988) *Vet Clin North Am Equin Pract* 4:105-113).

This highlights one of the competing imperatives in formulating a treatment protocol. On the one hand, reduction in bacteremia is required whereas such a treatment step can lead to greater release of endotoxin. There is a need to manage these treatment imperatives.

The endotoxin induces a cytokine mediated inflammatory response. Horses are particularly sensitive to endotoxin-mediated sepsis. The horse gut contains a high level of LPS from Gram-negative bacteria. The LPS is generally confined to the gut by an intestinal mucosal barrier composed of epithelial cells and the tight junctions between them. Cellular secretions and lamina propria also efficiently restrict the movement of bacteria and endotoxin (van Deventer et al. (1988) *Gastroenterology* 94:825-831). Compromise of the integrity of this barrier following an inflammatory condition or ischemia of the intestinal wall can lead to bacteremia and release of endotoxin to the blood system. This can also occur following severe local or disseminated infection in the gut (Woolcock (1985) *Aust Vet J* 62:177-181; Ziegler (1988) In Wyngaarden and Smith, eds. Cecil Textbook of Medicine $18^{th}$ ed. Philadelphia: WB Saunders 1658-1661).

Treatment is generally predicated on identification and alleviation of the causative disorder and therapeutic intervention to minimize the effects of septic shock. In the absence of suitable treatment, organ dysfunction subsequent to microvascular thrombosis and acid-base and electrolyte imbalance can occur, leading to significantly poor outcomes including death. This is a potentially significant issue in horse management in the racing industry where horses can be worth millions of dollars. In terms of the competing imperatives, antimicrobial therapy does not lead to direct mitigation of the effects of the endotoxin (McCue (1985) *Arch Intern Med* 145:1212-1216; Balis et al. (1979) *Lab Invest* 40:55-65) and, as indicated above, can lead to further endotoxin release (Shenep et al. (1988) *J Infect Dis* 157: 565-568), thereby exacerbating the inflammatory response.

Treatment options have hitherto been based on pharmacologic agents directed to blocking the inflammatory effects of endotoxins, immunotherapy directed to the endotoxin itself and antimicrobial therapy to reduce bacteremia (Morris (1991) *J Vet Int Med* 5:167-181). Whilst some of these treatment options have evidentiary basis, none on its own has been totally effective.

Part of the obstacle to therapy has been the comparison between endotoxemia in horses and systemic inflammatory response syndrome (SIRS) in humans. Whilst on one level, there are physiological similarities in the inflammatory response, there are a number of differences between these two species. In horses, for example, due to anatomical reasons, endotoxemia most commonly results from damage to the wall of the large intestine such as following colitis or intestinal strangulation. As indicated above, this compromises the gut mucosal barrier enabling release of endotoxin to the blood stream. As herbivores, horses not only have long hindgut anatomy which increases the risk of intestinal strangulation, they also have a different bacterial gut flora compared to humans. SIRS in humans, on the other hand, is less anatomically influenced and commonly results from infection, trauma, burns, pancreatitis and a variety of other injuries (Balk (2014) *Virulence* 5(1):20-26) Hence, the range of toxins and their effects differ between horses and humans. In consequence, the immune response also differs between horses and humans (see Review by Moore and Vandenplas (2014) *Vet Clin Equine* 30:337-351 which summarizes the difference in pattern-associated molecular patterns between horses and humans).

Therefore, drugs and therapeutic protocols which might appear useful based on the human experience with SIRS, may not be useful in horses to treat endotoxemia. This is particularly the case due to interspecies differences in dose sensitivity. An effective dose in one species may not equate to another species (Fehr et al. (2015) *Cell Physiol Biochem* 36:2237-2249).

Another troublesome inflammatory disorder in horses is laminitis, that is, inflammatory of the laminae of the hoof. This can be so severe that euthanasia is the only option.

Hence, there is a need to develop a therapeutic protocol specific for equine animals to mitigate the effects of inflammation.

SUMMARY

The present invention provides a method for treating an inflammatory condition in an equine animal. In one embodiment, the inflammatory condition is endotoxemia. By "treating endotoxemia" means treating the condition or an equine animal having symptoms of endotoxemia or a condition which could lead to endotoxemia or a complication arising from endotoxemia. Other inflammatory conditions include laminitis and postoperative ileus. The equine animal includes but is not limited to a horse. The method comprises the administration of a p38 mitogen-activated protein kinase (p38 MAPK) inhibitor or a pharmaceutically acceptable salt, prodrug or solvate thereof. In an embodiment, the p38 MAPK is formulated for parenteral administration such as via intravenous injection. Dosing will vary depending on the condition, however, in an embodiment, multiple doses of from 1 to 10 doses administered at from 6 to 60 hours apart are provided to the animal.

In an embodiment, the p38 MAPK inhibitor is 1-[5-tert-butyl-2-p-tolyl-2H-pyrazol-3-yl]-3-[4-(2-morpholin-4-yl-ethoxy)naphthalen-1-yl]-urea also referred to as BIRB-796 and doramapimod or a pharmaceutically acceptable salt, prodrug or solvate thereof.

Other p38 MAPK inhibitors include VX-745, VX-702, RO-4402257, SC10-469, SD-0006, PH-797804, AMG-548, SB-681323, LY2228820, GW-856553, SB202190, Skepinone-L, pexmetinib, SB239063, GDC-0994, SB203580, SB202190, Losmapimod and TAK-715 or their pharmaceutically acceptable salts, pro-drugs or solvates.

Further contemplated herein is a parenteral formulation for the treatment of endotoxemia in an equine animal. An animal may also be a candidate for endotoxemia treatment where the animal exhibits symptoms of a condition selected from the group consisting of laminitis, postoperative ileus, acute abdominal disease, colitis, peritonitis, pleuropneumonia, metritis, effects of exertion, septicaemia, recurrent airway obstruction, inflammatory airway disease and exercise-induced pulmonary hemorrhage. Such condition can lead to endotoxemia or a complication of endotoxemia.

Also enabled herein is a use of a p38 MAPK inhibitor in the manufacture of a medicament for the treatment of endotoxemia, symptoms of endotoxemia, a condition leading to endotoxemia or a complication arising from endotoxemia in an equine animal.

Further enabled herein is a use of a p38 MAPK inhibitor in the manufacture of a medicament for the treatment of laminitis, symptoms of laminitis, a condition leading to laminitis or a complication arising from laminitis in an equine animal.

Still further taught herein is a use of a p38 MAPK inhibitor in the manufacture of a medicament for the treatment of postoperative ileus, symptoms of postoperative ileus, a condition leading to postoperative ileus or a complication arising from postoperative ileus in an equine animal.

DETAILED DESCRIPTION

Figure 1:
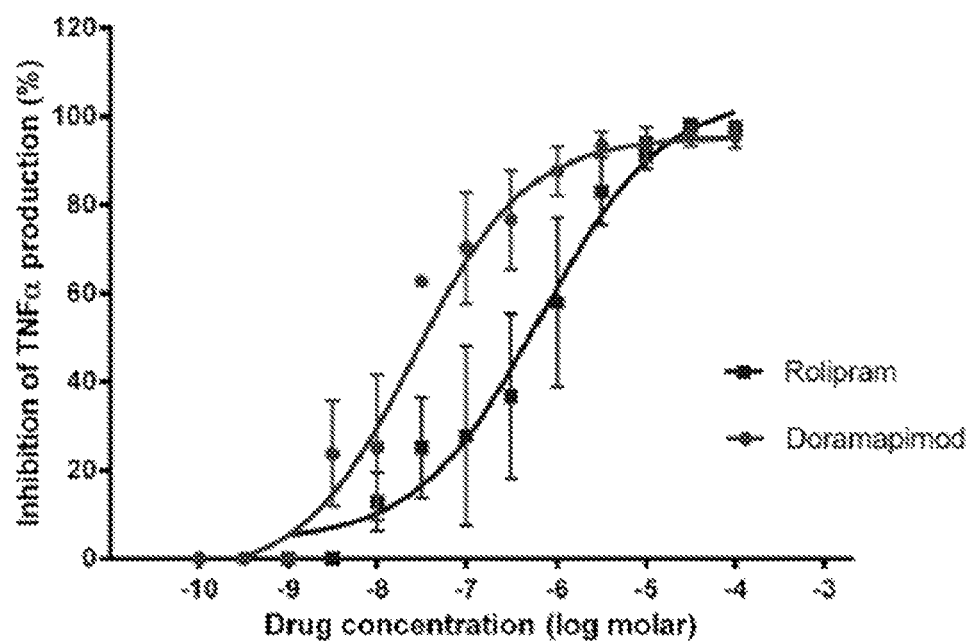
FIG. 1 is a graphical representation showing the effect of doramapimod and rolipram on inhibition of TNF production from whole blood stimulated with 1 µg/ml LPS.

Throughout this specification, unless the context requires otherwise, the word "comprise", or variations such as "comprises" or "comprising", will be understood to imply the inclusion of a stated element or integer or method step or group of elements or integers or method steps but not the exclusion of any other element or integer or method steps or group of elements or integers or method steps.

It is to be understood that unless otherwise indicated, the subject disclosure is not limited to specific formulation components, manufacturing methods, dosage regimens, or the like, as such may vary. It is also to be understood that the terminology used herein is for the purpose of describing particular embodiments only and is not intended to be limiting.

As used in the subject specification, the singular forms "a", "an" and "the" include plural aspects unless the context clearly dictates otherwise. Thus, for example, reference to "a symptom of endotoxemia" includes a single symptom, as well as two or more symptoms; reference to "an endotoxin" includes a single type of endotoxin, as well as two or more endotoxin types; reference to "the disclosure" includes single and multiple aspects taught by the disclosure; and so forth. Aspects taught and enabled herein are encompassed by the term "invention". Any variants and derivatives contemplated herein are encompassed by "forms" of the invention. All aspects of the invention are enabled across the width of the claims.

The present invention provides a therapeutic protocol to treat inflammation in equine animals. The therapeutic protocol comprises mitigating the inflammatory response through use of a p38 mitogen-activated protein kinase (p38 MAPK) inhibitor. Conditions include endotoxemia, laminitis and postoperative ileus. The agent used in the treatment of endotoxemia or other conditions may not necessarily be selected on the basis of being a p38 MAPK inhibitor although it is proposed that it would have this property. The treatment protocol includes mitigating endotoxemia and ameliorating symptoms thereof as well as being used in a prophylactic sense to prevent potential endotoxia in an equine animal having a disease or condition which could lead to endotoxemia. Hence, the current method of treatment includes a method of prophylaxis. The protocol optionally further comprises reducing the level of bacteremia and alleviating the original cause of the compromised intestinal mucosal barrier. In this regard, the protocol includes in one embodiment a method of treatment by the administration of a p38 MAPK inhibitor as well as a method of treatment comprising:

(i) diagnosis of a condition which has the potential to or has resulted in a compromised (i.e. leaky) gut mucosal barrier;
(ii) treating endotoxemia or potential endotoxemia;
(iii) treating bacteremia or potential bacteremia; and
(iv) treating the condition diagnosed under step (i).

The division of the protocol into individual steps is not to impugn any mandatory order in execution of these steps. Any of (i) through (iv) may be performed in any order provided at least step (ii) is performed. A similar protocol is proposed for the treatment of laminitis and postoperative ileus.

Hence, enabled herein is a method for treating endotoxemia in an equine animal, the method comprising administering to the equine animal an effective amount of a p38 mitogen-activated protein kinase (MAPK) inhibitor for a time and under conditions sufficient to ameliorate symptoms of endotoxemia in the equine animal. Further enabled herein is a method for treating laminitis in an equine animal, the method comprising administering to the equine animal an effective amount of a p38 mitogen-activated protein kinase (MAPK) inhibitor for a time and under conditions sufficient to ameliorate symptoms of laminitis in the equine animal. Still further enabled herein is a method for treating postoperative ileus in an equine animal, the method comprising administering to the equine animal an effective amount of a p38 mitogen-activated protein kinase (MAPK) inhibitor for a time and under conditions sufficient to ameliorate symptoms of postoperative ileus in the equine animal.

By "treating endotoxemia" includes treating the condition or symptoms of endotoxemia or a condition leading to endotoxemia or a complication arising from endotoxemia. Such a treatment, as indicated above, may be preventative such as in the case where an equine animal is diagnosed with a condition which could lead to endotoxemia. Such conditions include a microbial infection of the gut, intestinal strangulation, trauma or injury to the gut or an inflammatory condition of the gut such as colitis, pancreatitis or infection of inflammation of the epithelial layer of the large or small intestine, including cecum and colon. Reference to an "equine animal" includes a horse, a Przewalski horse, a zebra and an ass. A "horse" includes, but is not limited to, a Thoroughbred, Warmblood, Quarter Horse, Arabian, a Standardbred horse and a mixed breed horse. The terms "treating laminitis" and "treating postoperative ileus" have a similar meaning to "treating endotoxemia".

In an embodiment, the equine animal is a horse.

Hence, taught herein is a method for treating endotoxemia in a horse, the method comprising administering to the horse an effective amount of a p38 MAPK inhibitor for a time and under conditions sufficient to ameliorate symptoms of endotoxemia in the horse. By "treating endotoxemia" includes treating the condition, symptoms of endotoxemia, a condition leading to endotoxemia and/or a complication of endotoxemia. Reference to ameliorating symptoms of endotoxemia includes preventing or delaying development of symptoms.

In an embodiment, the p38 MAPK inhibitor is a compound of Formula (I):

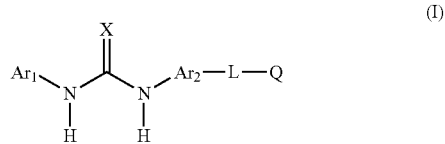

or a pharmaceutically acceptable salt, prodrug or solvate thereof,
wherein:
Ar$_1$ is selected from optionally substituted thiophene and optionally substituted pyrazole;
Ar$_2$ is selected from optionally substituted naphthyl, optionally substituted tetrahydronaphthyl, optionally substituted indanyl or optionally substituted indenyl;
L is C$_{1-6}$ saturated or unsaturated branched or unbranched carbon chain wherein one or more methylene groups are optionally independently replaced by O, N or S; and wherein the linking group is optionally substituted with 0-2 oxo groups and one or more C$_{1-4}$ branched or unbranched alkyl which may be substituted by one or more halogen atoms;
Q is selected from the group consisting of:
a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, C$_{1-6}$ alkyl, C$_{1-6}$ alkoxy, hydroxy, mono- or di-(C$_{1-3}$ alkyl)amino, C$_{1-6}$ alkyl-S(O)$_m$ and phenylamino wherein the phenyl ring is optionally substituted with one to two groups consisting of halogen, C$_{1-6}$ alkyl and C$_{1-6}$ alkoxy;
b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of C$_{1-6}$ alkyl, C$_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl; and c) $C_{1-6}$ alkoxy, secondary or tertiary amine wherein the amino nitrogen is covalently bonded to groups selected from the group consisting of $C_{1-3}$ alkyl, $C_{1-3}$ alkoxyalkyl and phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_r$, phenyl-S(O)$_r$, wherein the phenyl ring is optionally substituted with one to two groups consisting of halogen, $C_{1-6}$ alkoxy, hydroxy or mono- or di-($C_{1-3}$ alkyl)amino;

wherein:

m is an integer selected from 0, 1, 2;

r is an integer selected from 0, 1, 2; and t is an integer selected from 0, 1, 2.

In an embodiment, $AR_2$ is a naphthyl. In an embodiment, $Ar_1$ is pyrazole.

In an embodiment, L is selected from optionally substituted propoxy, optionally substituted ethoxy, optionally substituted methoxy, optionally substituted methyl, optionally substituted propyl, optionally substituted $C_{3-5}$ acetylene and optionally substituted methylamino.

In an embodiment, the compound is 1-[5-tert-butyl-2-p-tolyl-2H-pyrazol-3-yl]-3-[4-(2-morpholin-4-yl-ethoxy) naphthalen-1-yl]-urea (also referred to herein as BIRB-796 or doramapimod), or a pharmaceutically acceptable salt, prodrug or solvate thereof.

Accordingly, enabled herein is a method for treating endotoxemia in an equine animal, the method comprising administering to the equine animal an effective amount of a p38 MAPK inhibitor having the structure of Formula (I):

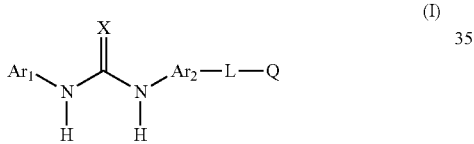

or a pharmaceutically acceptable salt, prodrug or solvate thereof, wherein:

$Ar_1$ is selected from optionally substituted thiophene and optionally substituted pyrazole;

$Ar_2$ is selected from optionally substituted naphthyl, optionally substituted tetrahydronaphthyl, optionally substituted indanyl or optionally substituted indenyl;

L is $C_{1-6}$ saturated or unsaturated branched or unbranched carbon chain wherein one or more methylene groups are optionally independently replaced by O, N or S; and wherein the linking group is optionally substituted with 0-2 oxo groups and one or more $C_{1-4}$ branched or unbranched alkyl which may be substituted by one or more halogen atoms; Q is selected from the group consisting of:

a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups consisting of halogen, $C_{1-6}$ alkyl and $C_{1-6}$ alkoxy;

b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl; and c) $C_{1-6}$ alkoxy, secondary or tertiary amine wherein the amino nitrogen is covalently bonded to groups selected from the group consisting of $C_{1-3}$ alkyl, $C_{1-3}$ alkoxyalkyl and phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_r$, phenyl-S(O)$_r$, wherein the phenyl ring is optionally substituted with one to two groups consisting of halogen, $C_{1-6}$ alkoxy, hydroxy or mono- or di-($C_{1-3}$ alkyl)amino;

wherein:

m is an integer selected from 0, 1, 2;

r is an integer selected from 0, 1, 2; and t is an integer selected from 0, 1, 2;

for a time and under conditions sufficient to ameliorate symptoms of endotoxemia in the equine animal.

In an embodiment, taught herein is a method for treating endotoxemia in a horse, the method comprising administering to the horse an effective amount of a p38 MAPK inhibitor having the structure of Formula (I):

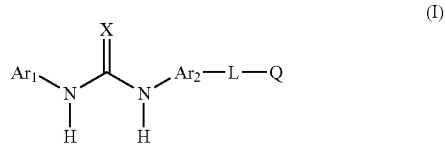

or a pharmaceutically acceptable salt, prodrug or solvate thereof, wherein:

$Ar_1$ is selected from optionally substituted thiophene and optionally substituted pyrazole;

$Ar_2$ is selected from optionally substituted naphthyl, optionally substituted tetrahydronaphthyl, optionally substituted indanyl or optionally substituted indenyl;

L is $C_{1-6}$ saturated or unsaturated branched or unbranched carbon chain wherein one or more methylene groups are optionally independently replaced by O, N or S; and wherein the linking group is optionally substituted with 0-2 oxo groups and one or more $C_{1-4}$ branched or unbranched alkyl which may be substituted by one or more halogen atoms; Q is selected from the group consisting of:

a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups consisting of halogen, $C_{1-6}$ alkyl and $C_{1-6}$ alkoxy;

b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl; and c) $C_{1-6}$ alkoxy, secondary or tertiary amine wherein the amino nitrogen is covalently bonded to groups selected from the group consisting of $C_{1-3}$ alkyl, $C_{1-3}$ alkoxyalkyl and phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_r$, phenyl-S(O)$_r$, wherein the phenyl ring is optionally substituted with one to two groups consisting of halogen, $C_{1-6}$ alkoxy, hydroxy or mono- or di-($C_{1-3}$ alkyl)amino;

wherein:
m is an integer selected from 0, 1, 2;
r is an integer selected from 0, 1, 2; and
t is an integer selected from 0, 1, 2,
for a time and under conditions sufficient to ameliorate symptoms of endotoxemia in the horse.

As indicated above, by "treating endotoxemia" includes treating the condition, symptoms of endotoxemia, a condition leading to endotoxemia and/or a complication of endotoxemia.

Further, enabled herein is a method for treating laminitis in an equine animal, the method comprising administering to the equine animal an effective amount of a p38 MAPK inhibitor having the structure of Formula (I):

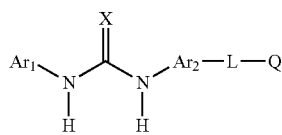

(I)

or a pharmaceutically acceptable salt, prodrug or solvate thereof,
wherein:
$Ar_1$ is selected from optionally substituted thiophene and optionally substituted pyrazole;
$Ar_2$ is selected from optionally substituted naphthyl, optionally substituted tetrahydronaphthyl, optionally substituted indanyl or optionally substituted indenyl;
L is $C_{1-6}$ saturated or unsaturated branched or unbranched carbon chain wherein one or more methylene groups are optionally independently replaced by O, N or S; and wherein the linking group is optionally substituted with 0-2 oxo groups and one or more $C_{1-4}$ branched or unbranched alkyl which may be substituted by one or more halogen atoms;
Q is selected from the group consisting of:
a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups consisting of halogen, $C_{1-6}$ alkyl and $C_{1-6}$ alkoxy;
b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl; and c) $C_{1-6}$ alkoxy, secondary or tertiary amine wherein the amino nitrogen is covalently bonded to groups selected from the group consisting of $C_{1-3}$ alkyl, $C_{1-3}$ alkoxyalkyl and phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_r$, phenyl-S(O)$_r$, wherein the phenyl ring is optionally substituted with one to two groups consisting of halogen, $C_{1-6}$ alkoxy, hydroxy or mono- or di-($C_{1-3}$ alkyl)amino;

wherein:
m is an integer selected from 0, 1, 2;
r is an integer selected from 0, 1, 2; and
t is an integer selected from 0, 1, 2;
for a time and under conditions sufficient to ameliorate symptoms of laminitis in the equine animal.

In an embodiment, taught herein is a method for treating postoperative ileus in a horse, the method comprising administering to the horse an effective amount of a p38 MAPK inhibitor having the structure of Formula (I):

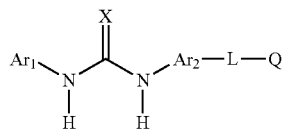

(I)

or a pharmaceutically acceptable salt, prodrug or solvate thereof,
wherein:
$Ar_1$ is selected from optionally substituted thiophene and optionally substituted pyrazole;
$Ar_2$ is selected from optionally substituted naphthyl, optionally substituted tetrahydronaphthyl, optionally substituted indanyl or optionally substituted indenyl;
L is $C_{1-6}$ saturated or unsaturated branched or unbranched carbon chain wherein one or more methylene groups are optionally independently replaced by O, N or S; and wherein the linking group is optionally substituted with 0-2 oxo groups and one or more $C_{1-4}$ branched or unbranched alkyl which may be substituted by one or more halogen atoms;
Q is selected from the group consisting of:
a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups consisting of halogen, $C_{1-6}$ alkyl and $C_{1-6}$ alkoxy;
b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl; and c) $C_{1-6}$ alkoxy, secondary or tertiary amine wherein the amino nitrogen is covalently bonded to groups selected from the group consisting of $C_{1-3}$ alkyl, $C_{1-3}$ alkoxyalkyl and phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_r$, phenyl-S(O)$_r$, wherein the phenyl ring is optionally substituted with one to two groups consisting of halogen, $C_{1-6}$ alkoxy, hydroxy or mono- or di-($C_{1-3}$ alkyl)amino;

wherein:

m is an integer selected from 0, 1, 2;

r is an integer selected from 0, 1, 2; and t is an integer selected from 0, 1, 2, for a time and under conditions sufficient to ameliorate symptoms of postoperative ileus in the horse.

The term "optionally substituted" means that a group may include one or more substituents. One or more hydrogen atoms on the group may be replaced by substituent groups independently selected from halogens (for example halo alkyl such as —CF$_3$ or —CF$_2$H), $C_{1-6}$ alkyl, $C_{2-6}$ alkenyl, $C_{2-6}$ alkynyl, —(CH$_2$)$_v$C$_{3-7}$ cycloalkyl, —(CH$_2$)$_v$C$_{4-7}$ cycloalkenyl, —(CH$_2$)$_v$ aryl, —(CH$_2$)$_v$ heterocyclyl, —(CH$_2$)$_v$ heteroaryl, —C$_6$H$_4$S(O)$_q$C$_{1-6}$ alkyl, C(Ph)$_3$, —CN, —OR, —O—(CH$_2$)$_{1-6}$—R, —O—(CH$_2$)$_{1-6}$—OR, —OC(O)R, —C(O)R, —C(O)OR, —OC(O)NR'R", —NR'R", —NO$_2$, —NRC(O)R', —NRC(O)NR'R", —NRC(S)NR'R", —NRS(O)$_2$R', —NRC(O)OR', —C(NR)NR'R", —C(=NOR')R, —C(=NOH)NR'R", —C(O)NR'R", —C(=NCN)—NR'R", —C(=NR)NR'R", —C(=NR')SR", —NR'C(=NCN)SR", —CONRSO$_2$R', —C(S)NR'R", —S(O)$_q$R, —SO$_2$NR'R", —SO$_2$NRC(O)R', —OS(O)$_2$R, —PO(OR)$_2$ and —NO$_2$; where v is 0-6, q is 0-2 and each R, R' and R" is independently selected from H, $C_{1-6}$ alkyl, $C_{2-6}$ alkenyl, $C_{2-6}$ alkynyl, $C_{3-7}$ cycloalkyl, $C_{4-7}$ cycloalkenyl, aryl, heterocyclyl, heteroaryl, $C_{1-6}$ alkylaryl, $C_{1-6}$ alkylheteroaryl, and $C_{1-6}$ alkylheterocyclyl, wherein the alkyl, alkenyl, alkynyl, cycloalkyl, cycloalkenyl, aryl, heterocyclyl, heteroaryl, $C_{1-6}$ alkylaryl, $C_{1-6}$ alkylheteroaryl, or $C_{1-6}$ alkylheterocyclyl, may be optionally substituted with one to six of same or different groups selected from halogen, hydroxy, lower alkyl, lower alkoxy, —CO$_2$H, CF$_3$, CN, phenyl, NH$_2$ and —NO$_2$; or when R' and R" are attached to the same nitrogen atom, they may, together with the atom to which they are attached, form a 5 to 7 membered nitrogen containing heterocyclic ring.

The term "alkyl" as used alone or in combination herein refers to a straight or branched chain saturated hydrocarbon group. The term "$C_{1-12}$ alkyl" refers to such a group containing from one to twelve carbon atoms and "lower alkyl" refers to $C_{1-6}$ alkyl groups containing from one to six carbon atoms, such as methyl ("Me"), ethyl ("Et"), n-propyl, isopropyl, n-butyl, isobutyl, sec-butyl, tert-butyl and the like.

The term "alkylene" refers to divalent alkyl groups preferably having from 1 to 10 carbon atoms and more preferably 1 to 6 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like. The term "alkoxy" as used alone or in combination refers to a straight or branched chain alkyl group covalently bound via an oxygen linkage (—O—) and the terms "$C_{1-6}$ alkoxy" and "alkyl alkoxy" refer to such groups containing from one to six carbon atoms, such as methoxy, ethoxy, propoxy, isopropoxy, butoxy, t-butoxy and the like.

The terms "halo" and "halogen" refers to fluoro, chloro, bromo and iodo groups.

The term "halo alkyl" group has one or more of the hydrogen atoms on an alkyl group replaced with halogens. Notable examples are —CF$_3$ or —CF$_2$H.

The term "alkylene" refers to divalent alkyl groups preferably having from 1 to 10 carbon atoms and more preferably 1 to 6 carbon atoms. Examples of such alkylene groups include methylene (—CH$_2$—), ethylene (—CH$_2$CH$_2$—), and the propylene isomers (e.g., —CH$_2$CH$_2$CH$_2$— and —CH(CH$_3$)CH$_2$—), and the like.

In an embodiment the optional substituents may be selected from: halogen (in particular, Cl, Br or F), $C_{1-6}$ alkyl, $C_{1-6}$ alkoxy, $C_{2-6}$ alkenyl, $C_{2-6}$ alkynyl, $C_{1-6}$ haloalkyl (in particular —CF$_3$), $C_{1-6}$ haloalkoxy (such as —OCF$_3$), —OH, phenyl, benzyl, phenoxy, benzyloxy, benzoyl, silyl, —NH$_2$, —NHC$_{1-4}$ alkyl, —N(C$_{1-4}$ alkyl)$_2$, —CN, —NO$_2$, mercapto, —P=O(OH)(NH$_2$), —S(O)$_2$NH$_2$, —S(O)$_2$NHC$_{1-4}$ alkyl, —S(O)$_2$N(C$_{1-4}$ alkyl)$_2$, $C_{1-6}$ alkylcarbonyl, $C_{1-6}$ alkoxycarbonyl, CO$_2$H, —S(O)R''' (where R''' is lower alkyl or cycloalkyl) and —S(O)$_2$R''' (where R''' is lower alkyl, cycloalkyl or OH).

In a embodiment, the optional substituents may be selected from: halogen (in particular, Cl, Br or F) and $C_{1-6}$ alkyl.

It will be appreciated that the compounds of the present invention, and the salts thereof, can be presented in the form of pharmaceutically acceptable derivatives. The term "pharmaceutically acceptable derivative" includes pharmaceutically acceptable esters, prodrugs, solvates and hydrates, or salts thereof. Pharmaceutically acceptable derivatives may include any pharmaceutically acceptable hydrate or any other compound or prodrug which, upon administration to an equine subject, is capable of providing (directly or indirectly) a compound having p38 MAPK inhibitor activity.

As used herein the expression "pharmaceutically acceptable salt" refers to the salt of a given compound, wherein the salt is suitable for administration as a pharmaceutical. For example, such salts may be formed by the reaction of an acid or a base with an amino or a carboxyl group respectively.

Pharmaceutically acceptable base addition salts may be prepared from inorganic and organic bases. Salts derived from inorganic bases include, but are not limited to, the sodium, potassium, lithium, ammonium, calcium, and magnesium salts. Salts derived from organic bases include, but are not limited to, salts of primary, secondary and tertiary amines, substituted amines including naturally-occurring substituted amines, and cyclic amines, including isopropylamine, trimethyl amine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, and N-ethylpiperidine. It should also be understood that other carboxylic acid derivatives would be useful in the practice of this invention, for example carboxylic acid amides, including carboxamides, lower alkyl carboxamides, di(lower alkyl) carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like.

In an embodiment, the p38 MAPK inhibitor is doramapimod.

Hence, taught herein is a method for treating endotoxemia in an equine animal, the method comprising administering to the equine animal an effective amount of doramapimod or a pharmaceutically acceptable salt, prodrug or solvate thereof for a time and under conditions sufficient to ameliorate symptoms of endotoxemia in the equine animal.

Further taught herein is a method for treating endotoxemia in a horse, the method comprising administering to the horse an effective amount of doramapimod or a pharmaceutically acceptable salt, prodrug or solvate thereof for a time and under conditions sufficient to ameliorate symptoms of endotoxemia in the horse.

As indicated above, by "treating endotoxemia" includes treating the condition, symptoms of endotoxemia, a condition leading to endotoxemia and/or a complication of endotoxemia.

Further enabled herein is a method for treating laminitis in an equine animal, the method comprising administering to the equine animal an effective amount of doramapimod or a pharmaceutically acceptable salt, prodrug or solvate thereof for a time and under conditions sufficient to ameliorate symptoms of laminitis in the equine animal.

Further taught herein is a method for treating postoperative ileus in a horse, the method comprising administering to the horse an effective amount of doramapimod or a pharmaceutically acceptable salt, prodrug or solvate thereof for a time and under conditions sufficient to ameliorate symptoms of postoperative ileus in the horse.

Reference to "doramapimod" or its other term such as BIRB-796, means a compound of Formula (II):

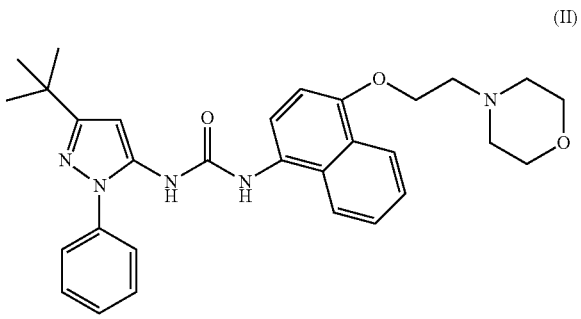 [SMILES: CC(C)(C)c1cc(NC(=O)Nc2ccc(OCCN3CCOCC3)c3ccccc23)n(-c2ccccc2)n1]

(II)

and includes pharmaceutically acceptable salts, prodrugs and solvates thereof as well as halogen-substituted derivatives thereof.

Other p38 MAPK inhibitors not necessarily encompassed by Formula I may alternatively be used. These include VX-745, VX-702, RO-4402257, SC10-469, SD-0006, PH-797804, AMG-548, SB-681323, LY2228820, GW-856553, SB202190, Skepinone-L, pexmetinib, SB239063, GDC-0994, SB203580, SB202190, Losmapimod and TAK-715 or their pharmaceutically acceptable salts, pro-drugs or solvates. Examples of these are disclosed in Xing (2015) *MAP Kinase* 4(5508):24-30 and in WO 2000/43384.

Hence, enabled herein is a method of treating endotoxemia in an equine animal, the method comprising administering to the equine animal an effective amount of a p38 MAPK inhibitor selected from the group consisting of VX-745, VX-702, RO-4402257, SC10-469, SD-0006, PH-797804, AMG-548, SB-681323, LY2228820, GW-856553, SB202190, Skepinone-L, pexmetinib, SB239063, GDC-0994, SB203580, SB202190, Losmapimod and TAK-715 or their pharmaceutically acceptable salts, pro-drugs or solvates thereof for a time and under conditions sufficient to ameliorate symptoms of endotoxemia in the equine animal.

Further enabled herein is a method for treating endotoxemia in a horse, the method comprising administering to the horse an effective amount of a p38 MAPK inhibitor selected from the group consisting of VX-745, VX-702, RO-4402257, SC10-469, SD-0006, PH-797804, AMG-548, SB-681323, LY2228820, GW-856553, SB202190, Skepinone-L, pexmetinib, SB239063, GDC-0994, SB203580, SB202190, Losmapimod and TAK-715 or a pharmaceutically acceptable salt, prodrug or solvate thereof for a time and under conditions sufficient to ameliorate symptoms of endotoxemia in the horse.

As indicated above, by "treating endotoxemia" includes treating the condition, symptoms of endotoxemia, a condition leading to endotoxemia and/or a complication of endotoxemia.

Further taught herein is a method of treating laminitis or postoperative ileus in an equine animal, the method comprising administering to the equine animal an effective amount of a p38 MAPK inhibitor selected from the group consisting of VX-745, VX-702, RO-4402257, SC10-469, SD-0006, PH-797804, AMG-548, SB-681323, LY2228820, GW-856553, SB202190, Skepinone-L, pexmetinib, SB239063, GDC-0994, SB203580, SB202190, Losmapimod and TAK-715 or their pharmaceutically acceptable salts, pro-drugs or solvates thereof for a time and under conditions sufficient to ameliorate symptoms of laminitis or postoperative ileus in the equine animal.

Further enabled herein is a method for treating laminitis or postoperative ileus in a horse, the method comprising administering to the horse an effective amount of a p38 MAPK inhibitor selected from the group consisting of VX-745, VX-702, RO-4402257, SCIO-469, SD-0006, PH-797804, AMG-548, SB-681323, LY2228820, GW-856553, SB202190, Skepinone-L, pexmetinib, SB239063, GDC-0994, SB203580, SB202190, Losmapimod and TAK-715 or a pharmaceutically acceptable salt, prodrug or solvate thereof for a time and under conditions sufficient to ameliorate symptoms of laminitis or postoperative ileus in the horse.

In an embodiment, the animal exhibits a condition selected from the group consisting of laminitis, postoperative ileus, acute abdominal disease, colitis, peritonitis, pleuropneumonia, metritis, effects of exertion, septicaemia, recurrent airway obstruction, inflammatory airway disease and exercise-induced pulmonary hemorrhage which lead to endotoxemia or which are a complication of endotoxemia.

In an embodiment, the symptoms of endotoxemia are selected from the group consisting of tachycardia, tachypnea, fever, discolored mucus membrane, prolonged capillary refill tine, dehydration and decreased gastrointestinal borborygmi.

Pharmaceutical compositions comprising a p38 MAPK inhibitor are conveniently prepared according to conventional pharmaceutical compounding techniques. See, for example, Remington's Pharmaceutical Sciences (1990) 18th Ed., Mack Publishing, Company. These compositions may comprise, in addition to an active substance (a p38 MAPK inhibitor), a pharmaceutically acceptable excipient, carrier, buffer, stabilizer or other materials well known in the art. Such materials should be non-toxic and should not interfere with the efficacy of the p38 MAPK inhibitor. The carrier may take a wide variety of forms depending on the form of preparation desired for administration, e.g. parenteral. In an embodiment, the formulation comprises a cyclodextrin to facilitate solubility and/or absorption (e.g. see US Publication No. 20030068340).

The p38 MAPK inhibitor as herein described or compositions comprising same are administered in an effective amount. The terms "effective amount" includes "therapeutically effective amount" and "prophylactically effective amount" and mean a sufficient amount of active either in a single dose or as part of a series or slow release system which provides the desired therapeutic, preventative, or physiological effect in an equine subject. Undesirable effects, e.g. side effects, may sometimes manifest along with the desired therapeutic effect; hence, a veterinarian balances the potential benefits against the potential risks in determining an appropriate "effective amount". The exact amount of composition required will vary from equine subject to equine subject, depending on age and general condition of the animal, mode of administration and the like. Thus, it may not be possible to specify an exact "effective amount". However, an appropriate "effective amount" in any case may be determined by one of ordinary skill in the art using routine skills or experimentation. The term "treatment" refers to any measurable or statistically significant amelioration in an equine subject in one or more symptoms of a condition associated with endotoxemia as defined herein. Prophylactic administration of the p38 MAPK inhibitor serves to prevent or attenuate onset of symptoms of endotoxemia should an equine animal have a condition (e.g. trauma, gut inflammation or infection) which could lead to endotoxemia.

A "pharmacologically acceptable" composition is one tolerated by a recipient equine animal. A "pharmaceutically acceptable carrier and/or a diluent" is a pharmaceutical vehicle comprised of a material that is not otherwise undesirable i.e. it is unlikely to cause a substantial adverse reaction by itself or with the active composition. Carriers may include all solvates, dispersion media, coatings, antibacterial and antifungal agents, agents for adjusting tonicity, increasing or decreasing absorption or clearance rates, buffers for maintaining pH, chelating agents, membrane or barrier crossing agents. A pharmaceutically acceptable salt is a salt that is not otherwise undesirable. The agent or composition comprising the agent may be administered in the form of pharmaceutically acceptable non-toxic salts, such as acid addition salts or metal complexes.

For parenteral administration, the composition may be dissolved in a carrier and administered as a solution or a suspension. For transmucosal or transdermal (including patch) delivery, appropriate penetrants known in the art are used for delivering the composition. For inhalation, delivery uses any convenient system such as dry powder aerosol, liquid delivery systems, air jet nebulizers, propellant systems. For example, the formulation can be administered in the form of an aerosol or mist. The compositions may also be delivered in a sustained delivery or sustained release format. For example, biodegradable microspheres or capsules or other polymer configurations capable of sustained delivery can be included in the formulation. Formulations can be modified to alter pharmacokinetics and biodistribution. For a general discussion of pharmacokinetics, see, e.g., Remington's Pharmaceutical Sciences, 1990 (supra). In an embodiment the formulation is incorporated in lipid monolayers or bilayers such as liposomes or micelles. Targeting therapies known in the art may be used to deliver the agents more specifically to certain types of cells or tissues.

The pharmaceutical forms suitable for injectable use include sterile aqueous solutions, sterile powders for the extemporaneous preparation of sterile injectable solutions and inhalable forms. Such forms are generally stable under the conditions of manufacture and storage. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of surfactants. In many cases, it is useful to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the p38 MAPK inhibitor and carrier/diluent in the required amount in the appropriate solvent followed by sterilization or at least a process to reduce contaminating viruses, bacteria or other biological entities to acceptable levels for administration to an equine subject. In the case of sterile powders for the preparation of sterile injectable solutions, suitable methods of preparation include vacuum drying and the freeze-drying technique that yields a powder of active ingredient plus any additionally desired ingredient.

It is understood that the compounds of the present invention may exist in one or more stereoisomeric forms (eg enantiomers, diastereomers). The present invention includes within its scope all of these stereoisomeric forms either isolated (in for example enantiomeric isolation), or in combination (including racemic mixtures).

The terms "preventing" and "prophylaxis" as used herein refer to administering a medicament beforehand to avert or forestall the appearance of one or more symptoms of a disease or disorder. The person of ordinary skill in the medical art recognizes that the term "prevent" is not an absolute term. In the veterinary art it is understood to refer to the prophylactic administration of a drug to substantially diminish the likelihood or seriousness of a condition, or symptom of the condition and this is the sense intended in this disclosure. As used herein the terms "prevent", "preventing" and "prevention" with regard to endotoxemia, refer to averting the cause, effects, symptoms or progression of endotoxemia prior to the disease or symptoms thereof fully manifest.

The terms "administer", "administering" or "administration" in reference to a p38 MAPK inhibitor or composition or formulation comprising same means introducing the compound into an equine animal. When a p38 MAPK inhibitor is provided in combination with one or more other active agents, "administration" and its variants are each understood to include concurrent and/or sequential introduction of the compound and the other active agents.

Hence, enabled herein is a method for treating endotoxemia in an equine animal, the method comprising parentally administering to the equine animal an effective amount of a p38 MAPK inhibitor for a time and under conditions sufficient to ameliorate symptoms of endotoxemia in the equine animal.

As indicated above, by "treating endotoxemia" includes treating the condition, symptoms of endotoxemia, a condition leading to endotoxemia and/or a complication of endotoxemia.

Hence, enabled herein is a method for treating laminitis or postoperative ileus in an equine animal, the method comprising parentally administering to the equine animal an effective amount of a p38 MAPK inhibitor for a time and under conditions sufficient to ameliorate symptoms of laminitis or postoperative ileus in the equine animal.

In an embodiment, the equine animal is a horse.

In an embodiment, administration via parenteral administration is by multiple doses of from 1 to 10 doses from about 6 hours to 60 hours apart. This includes 1, 2, 3, 4, 5, 6, 7, 8, 9 or 10 doses separated by 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59 or 60 hours. In an embodiment, 3 doses given approximately 24 hours apart.

In an embodiment, the parenteral administration is via intravenous injection.

As indicated above, the p38 MAPK inhibitor for parenteral administering is a compound of Formula (I):

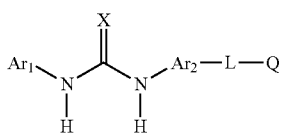

(I)

or a pharmaceutically acceptable salt, prodrug or solvate thereof,
wherein:
$Ar_1$ is selected from optionally substituted thiophene and optionally substituted pyrazole;
$Ar_2$ is selected from optionally substituted naphthyl, optionally substituted tetrahydronaphthyl, optionally substituted indanyl or optionally substituted indenyl;
L is $C_{1-6}$ saturated or unsaturated branched or unbranched carbon chain wherein one or more methylene groups are optionally independently replaced by O, N or S; and wherein said linking group is optionally substituted with 0-2 oxo groups and one or more $C_{1-4}$ branched or unbranched alkyl which may be substituted by one or more halogen atoms;
Q is selected from the group consisting of:

a) phenyl, naphthyl, pyridine, pyrimidine, pyridazine, imidazole, benzimidazole, furan, thiophene, pyran, naphthyridine, oxazo[4,5-b]pyridine and imidazo[4,5-b]pyridine, which are optionally substituted with one to three groups selected from the group consisting of halogen, $C_{1-6}$ alkyl, $C_{1-6}$ alkoxy, hydroxy, mono- or di-($C_{1-3}$ alkyl)amino, $C_{1-6}$ alkyl-S(O)$_m$ and phenylamino wherein the phenyl ring is optionally substituted with one to two groups consisting of halogen, $C_{1-6}$ alkyl and $C_{1-6}$ alkoxy;

b) tetrahydropyran, tetrahydrofuran, 1,3-dioxolanone, 1,3-dioxanone, 1,4-dioxane, morpholine, thiomorpholine, thiomorpholine sulfoxide, thiomorpholine sulfone, piperidine, piperidinone, tetrahydropyrimidone, cyclohexanone, cyclohexanol, pentamethylene sulfide, pentamethylene sulfoxide, pentamethylene sulfone, tetramethylene sulfide, tetramethylene sulfoxide and tetramethylene sulfone which are optionally substituted with one to three groups selected from the group consisting of $C_{1-6}$ alkyl, $C_{1-6}$ alkoxy, hydroxy, mono- or di-($C_{1-3}$ alkyl)amino-$C_{1-3}$ alkyl, phenylamino-$C_{1-3}$ alkyl and $C_{1-3}$ alkoxy-$C_{1-3}$ alkyl;

c) $C_{1-6}$ alkoxy, secondary or tertiary amine wherein the amino nitrogen is covalently bonded to groups selected from the group consisting of $C_{1-3}$ alkyl, $C_{1-3}$ alkoxyalkyl and phenyl wherein the phenyl ring is optionally substituted with one to two halogen, $C_{1-6}$ alkoxy, hydroxy or mono- or di-($C_{1-3}$ alkyl)amino, $C_{1-6}$ alkyl-S(O)$_r$, phenyl-S(O)$_r$, wherein the phenyl ring is optionally substituted with one to two groups consisting of halogen, $C_{1-6}$alkoxy, hydroxy or mono- or di-($C_{1-3}$ alkyl)amino;
m is an integer selected from 0, 1, 2;
r is an integer selected from 0, 1, 2; and
t is an integer selected from 0, 1, 2.

In an embodiment, the p38 MAPK inhibitor is doramapimod or a pharmaceutically acceptable salt, prodrug or solvate thereof.

In an embodiment, the p38 MAPK inhibitor is selected from the group consisting of VX-745, VX-702, RO-4402257, SCIO-469, SD-0006, PH-797804, AMG-548, SB-681323, LY2228820, GW-856553, SB202190, Skepinone-L, pexmetinib, SB239063, GDC-0994, SB203580, SB202190, Losmapimod and TAK-715 or their pharmaceutically acceptable salts, pro-drugs or solvates.

The compounds of this invention may be administered alone or in combination with adjuvants that enhance stability of the inhibitors, facilitate administration of pharmaceutic compositions containing them in certain embodiments, provide increased dissolution or dispersion, increase inhibitory activity, provide adjunct therapy, and the like, including other active ingredients. Advantageously, such combination therapies utilize lower dosages of the conventional therapeutics, thus avoiding possible toxicity and adverse side effects incurred when those agents are used as monotherapies. Compounds of the present invention may be physically combined with the conventional therapeutics or other adjuvants into a single pharmaceutical composition. Advantageously, the compounds may then be administered together in a single dosage form.

As mentioned above, dosage forms of the compounds of this invention include pharmaceutically acceptable carriers and adjuvants known to those of ordinary skill in the art. These carriers and adjuvants include, for example, ion exchangers, alumina, aluminium stearate, lecithin, serum proteins, buffer substances, water, salts or electrolytes and cellulose-based substances. Methods for preparing such dosage forms are known (see, for example, Ansel and Popovish (1990) *Pharmaceutical Dosage Forms and Drug Delivery Systems,* 5th ed., Lea and Febiger). Dosage levels and requirements are well-recognized in the art and may be selected by those of ordinary skill in the art from available methods and techniques suitable for a particular patient. In some embodiments, dosage levels range from about 0.1-100 mg/dose/kg animal. This includes 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or 100 mg/kg/animal. Although one dose from 6 to 60 hours apart (e.g. per day) may be sufficient, up to 10 doses per day may be given separated by these time periods. As the skilled artisan will appreciate, lower or higher doses may be required depending on particular factors. For instance, specific dosage and treatment regimens will depend on factors such as the equine animals general health profile, the severity and course of the animal's disorder or disposition thereto, and the judgment of the treating veterinarian.

In addition, the compounds of the present invention include prodrugs of compounds of the Formula (I). Prodrugs include those compounds that, upon simple chemical transformation, are modified to produce a compound of Formula (I). Simple chemical transformations include hydrolysis, oxidation and reduction. Specifically, when a prodrug of this invention is administered to a patient, the prodrug may be transformed into a compound of Formula (I), thereby imparting the desired pharmacological effect.

Further taught herein is the use of a parenteral formulation comprising a p38 MAPK inhibitor and one or more pharmaceutically acceptable carriers, excipients and/or diluents for use in treating endotoxemia or symptoms of endotoxemia. As indicated above, by "treating endotoxemia" includes treating the condition, symptoms of endotoxemia, a condition leading to endotoxemia and/or a complication of endotoxemia. Enabled herein is the use of a parenteral formulation comprising a p38 MAPK inhibitor and one or more pharmaceutically acceptable carriers, excipients and/or diluents for use in treating laminitis or postoperative ileus or symptoms of laminitis or postoperative ileus.

EXAMPLES

Aspects disclosed herein are further described by the following non-limiting Examples.

Two drugs, rolipram and doramapimod, were evaluated using in vitro whole blood assays where equine blood cells were stimulated with endotoxin in the presence or absence of the drugs. The safety/tolerance of the drugs was evaluated following a single intravenous injection and later a low-dose endotoxin challenge model was used in experimental horses, to simulate the diverse range of systemic inflammatory responses occurring in endotoxemia. The effects of the drugs were also evaluated on the clotting dysfunction caused by endotoxin.

The drug rolipram is one of the class of phosphodiesterase inhibitor drugs, causing an increase in levels of cyclic AMP, which reduces pro-inflammatory changes within leukocytes and platelets (involved in blood coagulation). It has anti-inflammatory effects on equine and human white blood cells in vitro.

Doramapimod is a drug which inhibits the key enzyme p38 MAPK, which is involved in cellular activation (leukocytes and platelets) caused by endotoxin.

Six adult healthy Standardbred horses (5 geldings and 1 mare) were used. The horses ranged in age from 5-12 years, and body weight from 460 to 520 kg. All horses underwent a complete veterinary examination prior to the commencement of the study including clinical biochemistry and hematology and no abnormalities were detected.

Example 1

Effect of Candidate Drugs on Cytokine Production

A whole blood assay was used to assess the effects of rolipram and doramapimod on cytokine production from leukocytes (white blood cells) in response to bacterial lipopolysaccharide (endotoxin).

Blood samples (10 mL; sodium citrate anticoagulant) were obtained from the six normal horses, diluted 1:1 with RPMI 1640 cell culture medium and aliquoted into 15×1 mL aliquots. Serial dilutions of rolipram and doramapimod were made from $10^{-2}$M stock solutions in phosphate-buffered saline and DMSO, respectively, and 10 µL added to 20 give final concentrations ranging from $10^{-10}$-$10^{-4}$ Molar. The samples were then incubated with 100 ng/mL purified bacterial lipopolysaccharide (endotoxin derived from *E. Coli* O55:B5; purified to remove DNA and protein contaminants). After incubation for 18 hours at 37° C. in a shaking incubator, samples were centrifuged at 300 g and supernatants stored at −80° C. for cytokine analysis.

The proinflammatory cytokine, TNF-α, was measured using a L929 fibrosarcoma cell bioassay. This cell line is sensitive to TNF-induced cell death, which was assayed using a MTT assay kit (TACS MTT cell proliferation assay; R&D Systems Inc., Minneapolis Minn.). The yellow tetrazole dye, 3-(4,5-dimethylthiazol-2-yl)-2,5-diphenyltetrazolium bromide (MTT), is reduced to a purple formazan compound in living cells, which is then quantified using a colorimetric plate reader (absorbance read at 570 nm with reference wavelength of 650 nm). Recombinant equine TNF-α, diluted in cell culture medium and an equivalent volume of blank equine plasma containing no detectable TNF-α, was used to produce the standard curve.

Plasma IL-1β concentrations were measured using an equine-specific enzyme linked immunosorbent assay (ELISA; Horse IL-1β ELISA kit, Bethyl Laboratories, Montgomery, Tex., USA). A standard curve was constructed using a known concentration of equine recombinant IL-1β. The ELISA kits were stored and used according to the manufacturer's instructions. The optical density (OD) values of samples were determined at 450 nm using an ELISA plate reader (BioTek Synergy H1) and concentrations determined using GENS Software (version 2.00.17).

The data are expressed as % inhibition of LPS-induced cytokine production at each of the drug concentrations. Concentration-response curves were generated from this data and fitted using Graphpad Prism software (Version 5.0). Values for maximum response and IC50 (the concentration of drug calculated to give a 50% inhibition of cytokine production) were derived from the curves.

Formulation for Intravenous Administration

Solubility of the drugs was tested to determine their suitability for intravenous administration (this is the route of choice for the treatment of endotoxemia). Where the drugs were not soluble in aqueous solutions (sterile 0.9% w/v saline), their solubility in DMSO, polyethylene glycol 400, kolliphor HS-15 (solutol) and 2-hydroxypropyl beta-cyclodextrin was assessed. Drug solutions were added to equine plasma in the laboratory to ensure that no precipitation of the drug occurred. Solutions were prepared in sterile cabinets and sterile filtered (0.22 µm filter) prior to intravenous administration to horses.

Preliminary Safety/Tolerance Study

Doramapimod was given to the 6 Standardbred horses at a dose of 0.5 mg/kg intravenously, dissolved in beta-cyclodextrin. Clinical parameters (heart rate, respiratory rate, rectal temperature, demeanor, mucous membrane color and capillary refill time, auscultation of gastrointestinal sounds, and indirect blood pressure) and white blood cell counts were monitored at baseline, then at 2, 5, 15, 30, 60, 90, 120, 180, 240, 300 and 360 min, and 24 hours after doramapimod administration. Hematology and biochemistry were performed on blood samples taken 24 hours after administration of doramapimod.

Pharmacodynamics and Pharmacokinetics

Pharmacodynamic analysis was performed by stimulating whole blood taken at the 10 above time points with lipopolysaccharide (LPS) at a final concentration of 1 µg/ml (including a stimulated baseline sample [positive control] and an unstimulated baseline sample [negative control]). Measurements of TNF-α were performed using the L929 fibrosarcoma bioassay. The inhibition of production of this cytokine was plotted against time.

Serial plasma samples were also stored for pharmacokinetic analysis of drug concentrations in the plasma using liquid chromatography-mass spectrometry (LC-MS).

Example 2

Anti-Inflammatory Effects of Doramapimod In Vivo: Low-Dose Endotoxin Challenge Model The main candidate drug was tested in an experimental model to stimulate some of the inflammatory changes seen in horses with naturally-occurring clinical disease. This well characterized model induces mild signs of malaise similar to transient 'flu-like' symptoms which resolve over 4-5 hours.

The study was conducted as a randomized, blinded crossover design, with each horse acting as its own control. The horses were pair matched by body weight: one horse was selected at random to receive the test product in the first experimental period, and the other received the placebo. The treatments were then crossed over for the second experimental period, so that each horse received both the treatment and vehicle placebo (half the horses receiving the treatment first). There was a three week washout period between challenges.

Doramapimod (0.5 mg/kg, intravenous) was administered immediately prior to the endotoxin infusion. The placebo control was the vehicle (cyclodextrin). The drug or placebo was administered by a different clinician so that the primary investigator remained blinded during the study.

The low-dose endotoxin challenge was conducted as previously described. Jugular venous catheters were placed, under local anaesthesia (2 ml of 2% w/v lignocaine; Ilium Lignocaine 20, Troy Laboratories Pty. Ltd., Smithfield, Australia). Sterile, filtered 10 endotoxin (*E. Coli* LPS O55: B5; 1.2 million endotoxin units/mg) was infused at a dose of 1 ng/kg/min, over 30 min (total dose 30 ng/kg; dissolved in 500 mL sterile saline), controlled by infusion pump (Baxter International Colleague CX, Sydney, Australia).

Clinical Assessments

Clinical outcomes including rectal temperature, heart rate, respiratory rate, intestinal sounds and demeanour were recorded immediately prior to pre-treatment and before LPS infusion, then every 15 min for 2 h, then every 30 min for the following 4 h. Blood was collected via the intravenous catheter at the same time points into tubes containing anticoagulant ethylenediaminetetraacetic acid (EDTA) and lithium heparin. Blood pressure was measured non-invasively using an oscillometric (tail cuff) technique, at 0 minutes, then at the 2 h time point (BpTRU Model BPM-300; VSM Medtech Ltd, Vancouver, Canada).

Horses were held in stocks (two horses side by side in separate stocks) in a covered building for the first 4 h, after which they were placed into a small concrete yard for a further 2 h and allowed hay and water ad libitum. At the 6 h time point, the experiment was completed; all horses then received flunixin meglumine (1.1 mg/kg intravenously) and were allowed back into their paddock. Additional checks and samples were conducted in the paddock after 24 h.

Blood Sample Analysis

Leukocyte counts were performed on whole blood samples using a Coulter Counter (model Z1; Coulter Electronics Inc). Plasma cytokine analysis was conducted as described above.

Effect of Candidate Drugs on Clotting Dysfunction

Clotting function was assessed in the low-dose endotoxin infusion model by obtaining samples at baseline and 2 hours after the start of the infusion. The prothrombin time (extrinsic clotting pathway) and the activated partial thromboplastin time (APTT; intrinsic and common coagulation pathways) were measured.

To evaluate the overall clotting function, including fibrin-platelet interaction, the strength of the clot and rate of clot lysis, a technique called thromboelastography (TEG) was used. This technique has been validated previously in horses with colic, and used to investigate the effects of endotoxemia in humans.

The TEG machine (5000 series TEG analyser; Hemoscope Corporation, Niles Ill. USA) physically records the adhesion of the clot to a central pin connected to a sensitive torsion gauge. The clotting sample is slowly rotated around the pin, and the stronger the clot the greater the pin is rotated. A chart tracing is obtained on the computer screen, and the following information is gathered:

R time (reaction time, minutes): the time from start of the analysis to clot initiation K time (minutes): the time for the TEG tracing to reach a set clot strength Ang (angle, degrees): indicator of the rate of clot formation MA (maximum amplitude, millimetres): the greatest clot strength achieved Ly30 (percent): clot lysis as determined by percent decrease in area under the curve compared to the MA at 30 minutes after MA is achieved.

Whole blood was collected from each of 6 healthy horses into 1.8 ml vacutainer tubes containing sodium citrate to a final concentration of 3.2%. LPS was added to give a final concentration of 10 μg/ml, with and without 1 μM doramapimod, and the samples incubated in a shaking water bath (37° C.) for 4 hours. Control samples were also run without addition of drugs or LPS, and samples were also run with the addition of the vehicle (cyclodextrin) only.

After incubation, 1 ml of the blood sample was added to a tube containing kaolin and 340 μL was then added to the TEG sample well (cup). 20 μL of 0.2M calcium chloride was added to the cup. TEG tracings were allowed to run until a Ly30 value had been obtained.

In the whole blood stimulation assays, both rolipram and doramapimod caused a concentration-dependant inhibition of TNFa production (FIG. 1). Both drugs caused near complete (~100%) inhibition at high concentrations. However, calculating the drug concentration that caused a 50% inhibition of cytokine production (the $IC_{50}$ value), 15 doramapimod inhibited cytokine production over a lower concentration range than rolipram, giving an $IC_{50}$ value of $2.61 \times 10^{-8}$ M. The $IC_{50}$ value for rolipram was $6.53 \times 10^{-7}$ M (rolipram curve lying to the right of doramapimod).

FIG. 1 depicts the effect of doramapimod and rolipram on inhibition of TNF production from whole blood stimulated with 1 μg/ml LPS. Each point represents mean±SEM from samples taken from 4 horses.

Rolipram and doramapimod also caused a concentration-dependant inhibition of IL-1 production (FIG. 2), although the degree of inhibition was not as pronounced as TNF. The maximum inhibition caused by doramapimod was 64.1±5.2% and the maximum inhibition caused by rolipram was 39.5±7.1%. Again, doramapimod inhibited the production of this cytokine over a lower concentration range than rolipram, giving an $IC_{50}$ value of $2.84 \times 10^{-8}$ M. The $IC_{50}$ value for rolipram was $1.02 \times 10^{-6}$ M (rolipram curve lying to the right of doramapimod).

Figure 2:
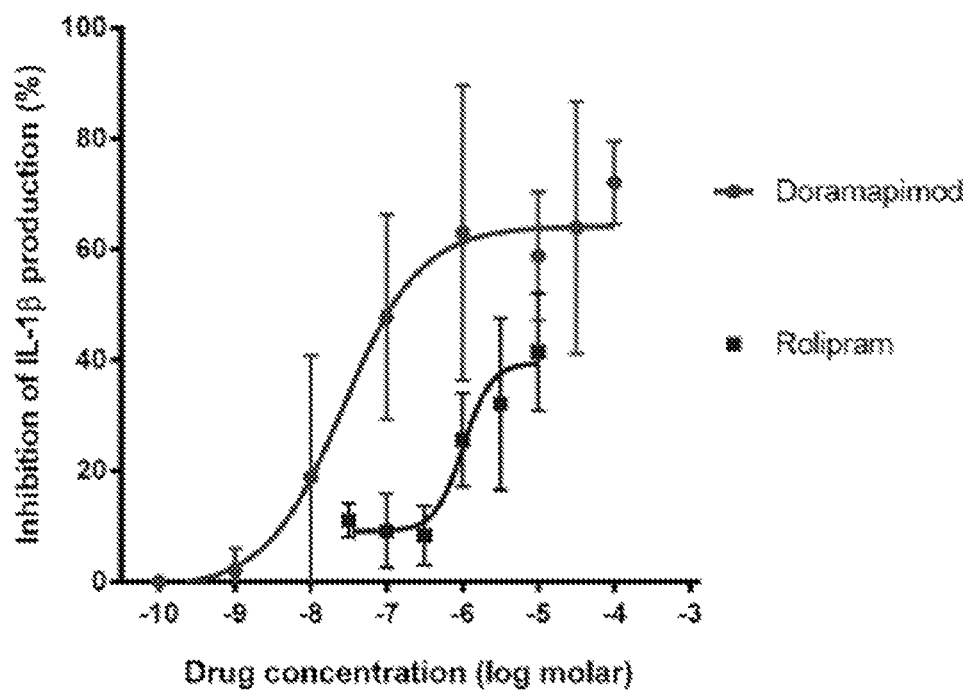
FIG. 2 is a graphical representation showing the effect of doramapimod and rolipram on inhibition of IL-1 production from whole blood stimulated with 1 µg/ml LPS.

FIG. 2 shows the effect of doramapimod and rolipram on inhibition of IL-1 production from whole blood stimulated with 1 μg/ml LPS. Each point represents mean±SEM from samples taken from 4 horses.

Formulation of Drugs for Intravenous Administration

Rolipram was water soluble to 0.2 mg/mL and soluble in 10% DMSO to 1 mg/mL and was suitable for injection in this form.

The water-insoluble drug, doramapimod is soluble in 2-hydroxypropyl beta-cyclodextrin, which has a ring-like molecular structure which can shield hydrophobic molecules and allow them to dissolve in aqueous solutions. A 1 mg/ml solution of doramapimod in 250 mg/mL 2-hydroxypropyl beta-cyclodextrin formed a stable solution which could be added to equine plasma in the laboratory with no precipitation. Therefore this formulation, once sterile filtered (0.22 μm filter), was suitable to be administered intravenously to horses.

Preliminary Safety/Tolerance Studies

Doramapimod was given to 6 Standardbred horses at a dose of 0.5 mg/kg intravenously, (dissolved in sterile saline containing beta-cyclodextrin as described above; volume 0.5 ml per Kg BW). No adverse effects were observed. All clinical parameters (heart rate, respiratory rate, rectal temperature, demeanour, mucous membrane color and capillary refill time, and gastrointestinal sounds) remained unchanged and completely normal in all horses (data not shown). White blood cell counts remained normal, including the sample taken 24 hours after doramapimod administration. Blood biochemistry parameters were also completely normal, 24 hours following the administration of doramapimod.

Pharmacodynamics and Pharmacokinetics

To assess the activity of the drug at plasma levels occurring after intravenous administration, pharmacodynamic analysis was performed by taking serial blood samples over 6 hours and stimulating them in the laboratory with lipopolysaccharide (LPS; 1 μg/mL) as described above. TNF- production by the stimulated leukocytes was used as the primary outcome. The results are shown in FIG. 3.

Immediately prior to administration of doramapimod, the time 0 blood sample produced 3505.5±322.2 pg/ml of TNF-; this was reduced to 252.3±56.9 pg/mL by the doramapimod concentrations in the blood stream sampled 2 mins after the drug was given. The effects of the drug were still markedly apparent after 6 hours, with a 53.3±27.2% inhibition of TNF-production still apparent at this time. With this degree and duration of anti-inflammatory effect following administration of 0.5 mg/kg doramapimod, it was decided that this was an appropriate dose to take forward into the in vivo low dose endotoxin challenge model.

Figure 3:
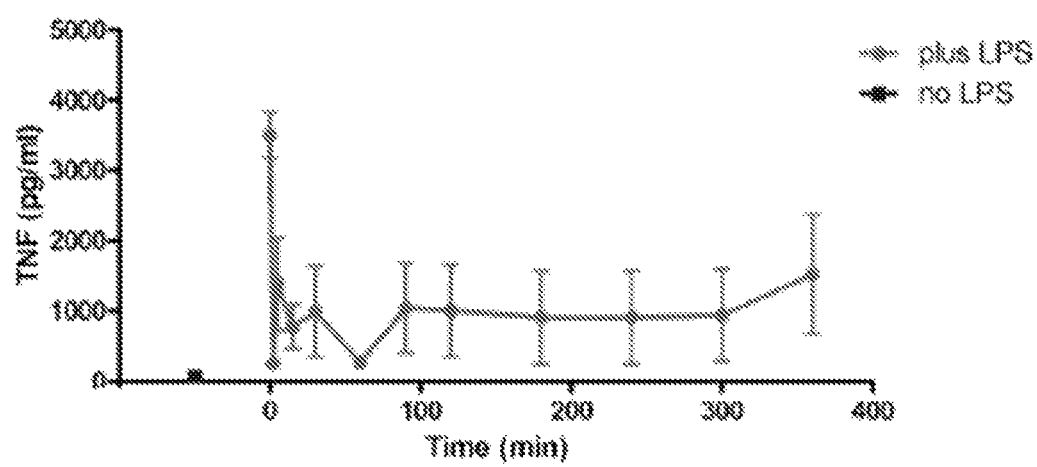
FIG. 3 is a graphical representation showing a bioassay for effect of doramapimod in blood samples taken after intravenous administration of 0.5 mg/kg.

FIG. 3 shows bioassay for effect of doramapimod in blood samples taken after intravenous administration of 0.5 mg/kg. Blood samples were stimulated with 1 μg/mL LPS for 18 h and TNF-production measured. Each point represents mean±SEM from 6 horses.

Anti-Endotoxaemic Effects of Doramapimod In Vivo: Low-Dose Endotoxin Challenge

The low-dose endotoxin challenge was well tolerated by all horses, and produced mild 'flu-like' symptoms which were only transient. However, measureable changes in clinical signs were observable, and also further objective evidence of systemic inflammation and leukocyte activation, which could be used to assess the anti-inflammatory effects of the drug doramapimod.

Clinical Signs

Figure 4:
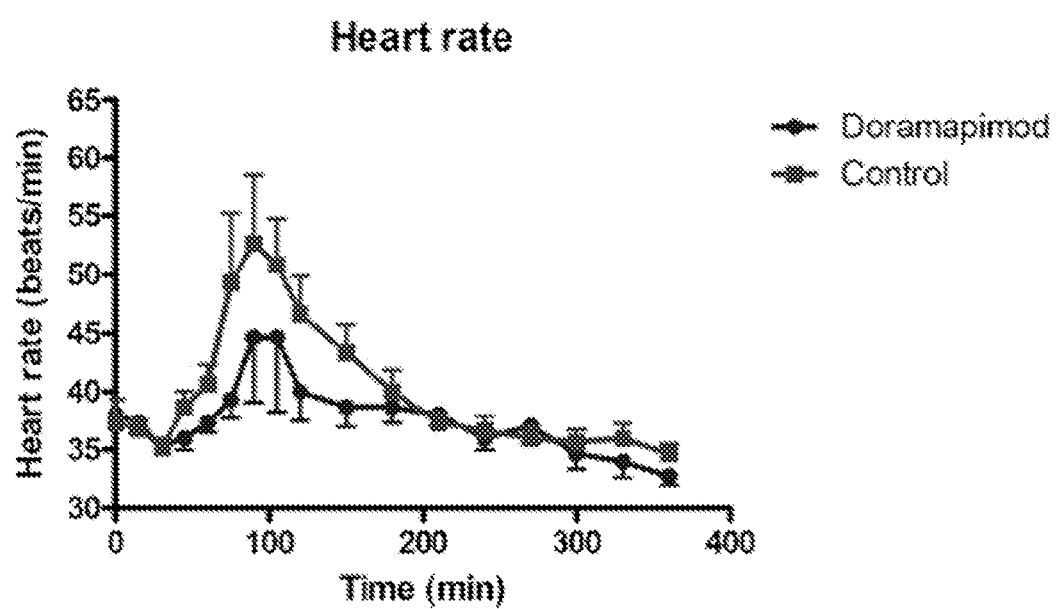
FIG. 4 is a graphical representation showing the effect of doramapimod on heart rate following LPS infusion.

The administration of lipopolysaccharide to normal horses caused a transient increase in heart rate which reached a peak at 90 min (mean±SEM of 54±5 beats/min) and returned to normal by 200 min (FIG. 4). Following pre-treatment with doramapimod, the peak heart rate was significantly reduced (47±6 beats/min) (paired t-test; P=0.021). The area under the curve for heart rate was also significantly lower for the doramapimod treatment group compared to controls (1050±336.4 compared with 1862±323.4 for the treated and control groups, respectively; P=0.046).

FIG. 4 shows the effect of doramapimod on heart rate following LPS infusion. Each point represents mean±sem from 6 horses.

Intestinal sounds were transiently reduced in response to the endotoxin infusion, and subjectively this decrease in intestinal motility was not as apparent when doramapimod had been given.

Figure 5:
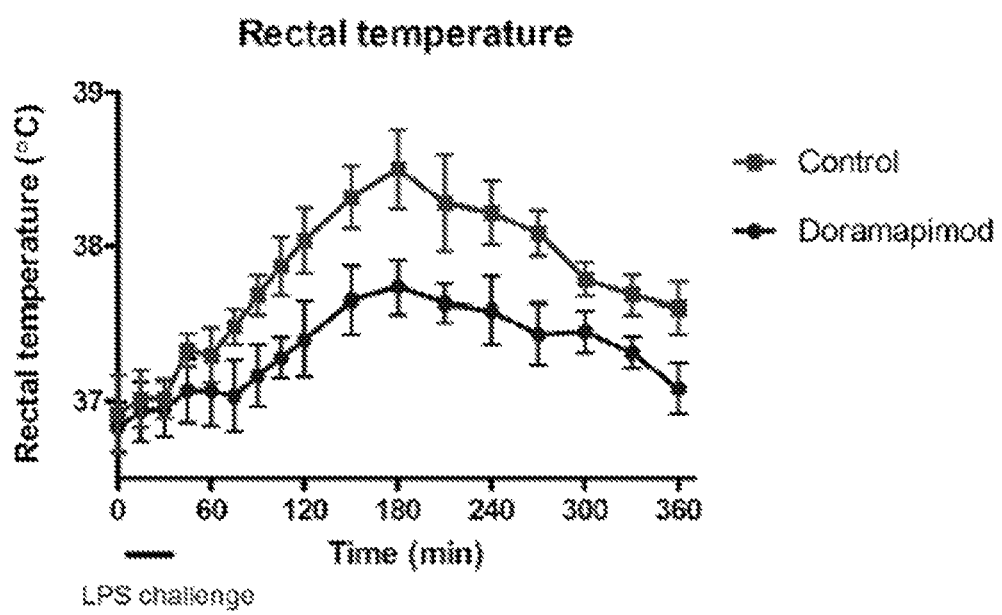
FIG. 5 is a graphical representation showing the effect of doramapimod on the response of rectal temperature to LPS infusion.

Rectal temperature is a very sensitive indicator of systemic inflammation and cytokine release in response to low-dose LPS infusion. Rectal temperature increased to 38.4±0.23° C. following vehicle administration (FIG. 5). After doramapimod administration, the peak rectal temperature was 37.8±0.16° C. While the difference in peak temperature was not significantly different between groups (P=0.154), the area under the curve was significantly lower in the doramapimod group (175.6±42.92 arbitrary units) compared to control values (344.2±67.49; P=0.020).

FIG. 5 shows the effect of doramapimod on the response of rectal temperature to LPS infusion. Each point represents mean±sem from 6 horses.

Changes in Blood Pressure

Figure 6:
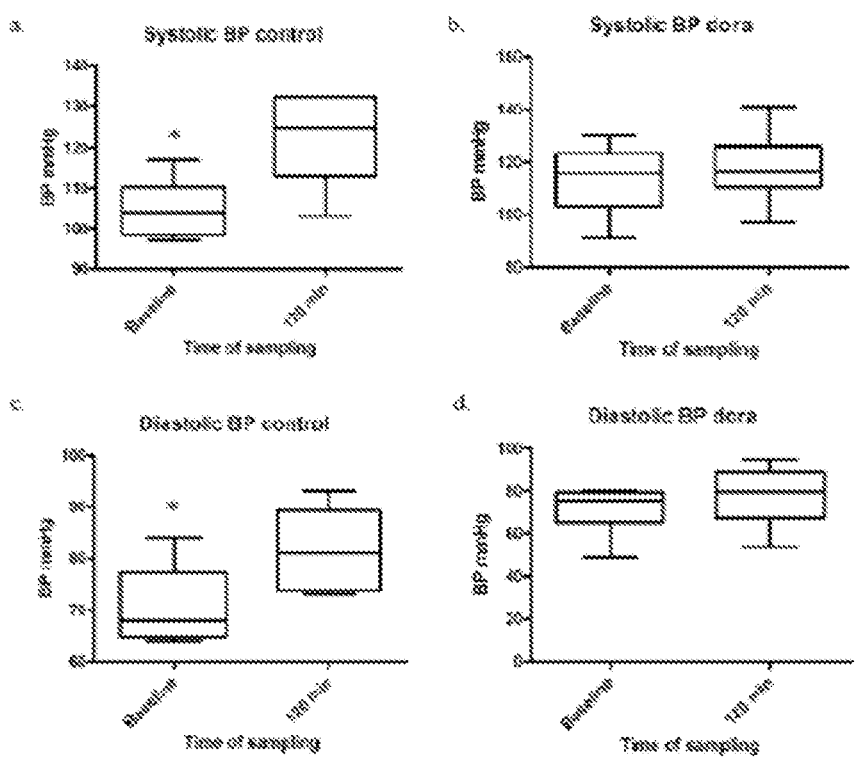
FIG. 6 is a graphical representation showing systolic and diastolic blood pressure measured non-invasively before and during the peak inflammatory phase of endotoxemia.

Endotoxin administration also caused a significant increase in both systolic and diastolic blood pressure (FIG. 6). The mean increase in systolic blood pressure was from 105 to 122 mmHg in the vehicle control group (P=0.003; panel a). However, following doramapimod treatment, there was no longer a significant increase in blood pressure (increase from 114 to 118 mmHg from baseline to 120 min; P=0.216; panel b). Similarly, for diastolic blood pressure, the increase observed between baseline and 120 minutes was not significant for the doramapimod group (mean increase from 72 to 78 mmHg for diastolic blood pressure; P=0.095; panel d), but was significant for the control group (mean increase from 71 to 82 mmHg for diastolic blood pressure; P=0.002; panel c).

FIG. 6 shows systolic (a and b) and diastolic blood pressure (c and d) measured non-invasively before and during the peak inflammatory phase of endotoxemia. Box and whisker plots represent median, interquartile range and range. * indicates significant difference (P<0.05).

Leukocyte Counts

Figure 7:
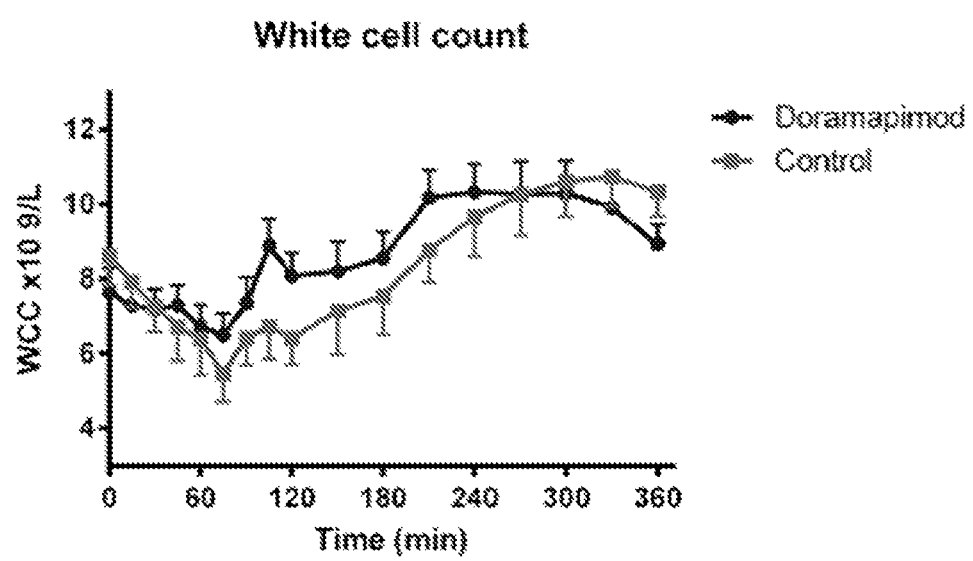
FIG. 7 is a graphical representation showing the effect of doramapimod on changes in blood leukocyte count in response to LPS infusion.

A transient decrease was observed in the white cell count, caused by the endotoxin infusion. This is due to the activation of both leukocytes and also endothelial cells lining blood vessels, causing leukocytes to adhere to the endothelium and leave the circulation. As the inflammatory stimulus wears off, the leukocytes detach and return to the circulating blood pool. As shown in FIG. 7, doramapimod treatment blunted the decrease in blood leukocyte count. The reduction in white blood cell count from baseline (delta change) was significantly greater in the vehicle group ($3.391±0.666×10^9$/L) compared to the doramapimod group ($1.296±0.36×10^9$/L; P=0.003). The white blood cell count nadir was also significantly lower in the vehicle group ($5.236±0.678×10^9$/L compared to $6.363±0.599×10^9$/L for the doramapimod group; P=0.003).

FIG. 7 shows the effect of doramapimod on changes in blood leukocyte count in response to LPS infusion. Each point represents mean±sem from 6 horses.

Plasma Pro-Inflammatory Cytokine Levels

Figure 8:
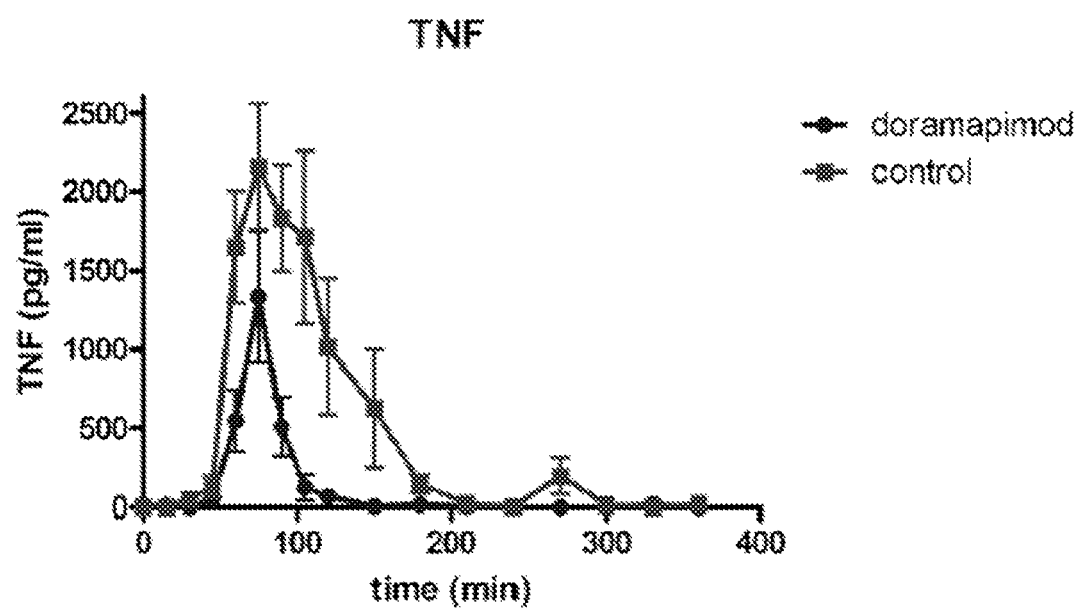
FIG. 8 is a graphical representation showing the effect of doramapimod on plasma TNF production in response to LPS infusion.

The 30 minute endotoxin infusion caused a sharp spike in plasma TNF-α concentration, peaking 75 min after the onset of the infusion and returning to baseline by 200 mins (FIG. 8). Following vehicle administration (control values), the peak concentration was 2276.2±447.5 pg/mL. Pre-treatment with doramapimod showed a strong trend towards reducing peak TNF concentrations (1381.7±391.9 pg/mL) but did not quite reach statistical significance (P=0.055; FIG. 8b). However, when comparing the AUC for TNF-α production (FIG. 8b), the overall amount of TNF-α produced was significantly diminished in the doramapimod group (43469±11474 arbitrary units compared to vehicle values of 189119±51413; P=0.033).

FIG. 8 shows the effect of doramapimod on plasma TNF production in response to LPS infusion. Each point represents mean±sem from 6 horses.

Effect of Doramapimod on Clotting Dysfunction

Figure 9:
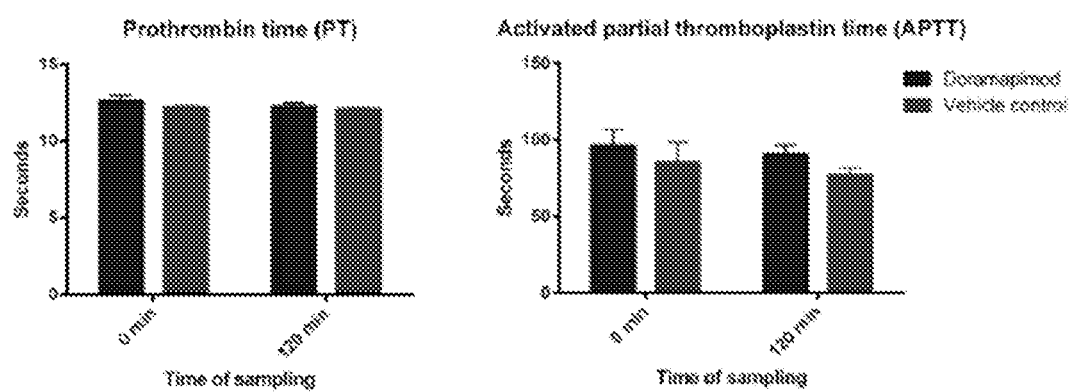
FIG. 9 is a graphical representation showing changes in clotting parameters observed during the low-dose endotoxin infusion model.

Because of the mild nature of the endotoxemia model used, the changes in clotting function that were observed were not statistically significant (FIG. 9). Prothrombin time, a measure of the extrinsic clotting pathway, was unchanged throughout the procedures; however there was a small numerical decrease (not significant) in the activated partial thromboplastin time (APTT) caused by the endotoxin (vehicle group decreased from 85.0±13.3 seconds to 76.9±4.4 s). Interestingly, doramapimod appeared to prevent this reduction in APTT (treatment group APTT 90.7±5.8 at 120 min), and there was a small trend when comparing values for doramapimod vs vehicle groups at 120 min (P=0.13; paired t-test).

Figure 10A:
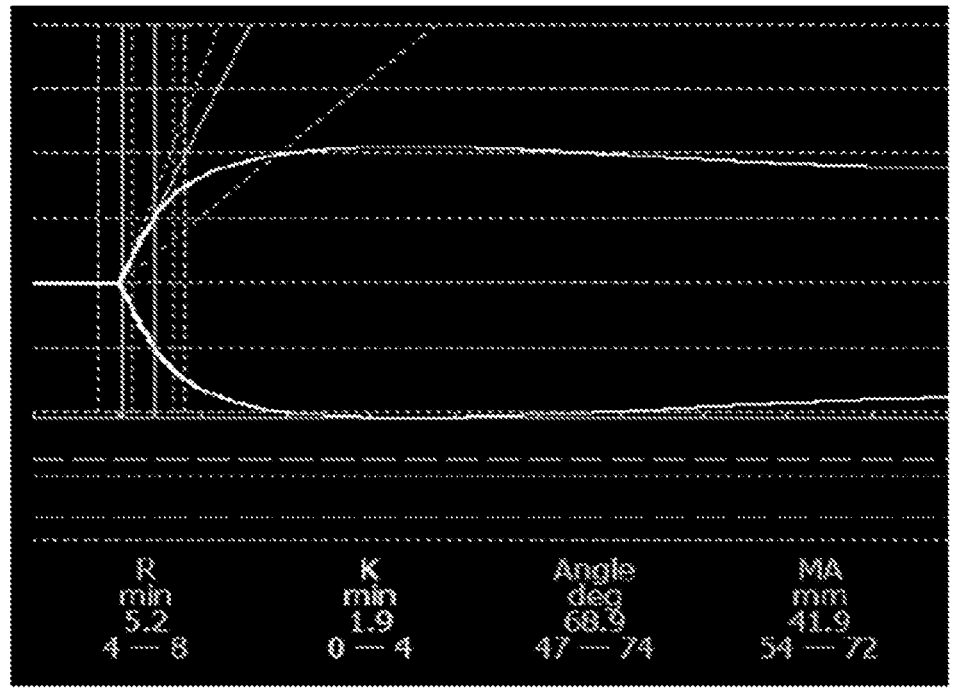
FIGS. 10a through 10c are photographical representations showing example tracings from one horse to show the effect of LPS (endotoxin) on whole blood clotting measured by thromboelastography (TEG), and the effect of doramapimod.
Figure 10B:
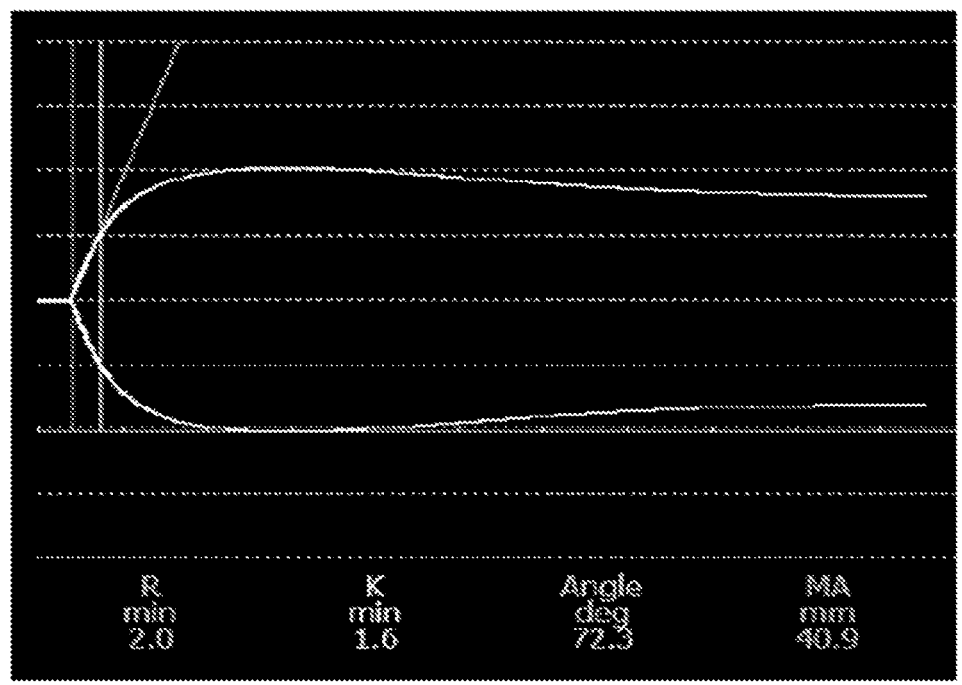
Figure 10C:
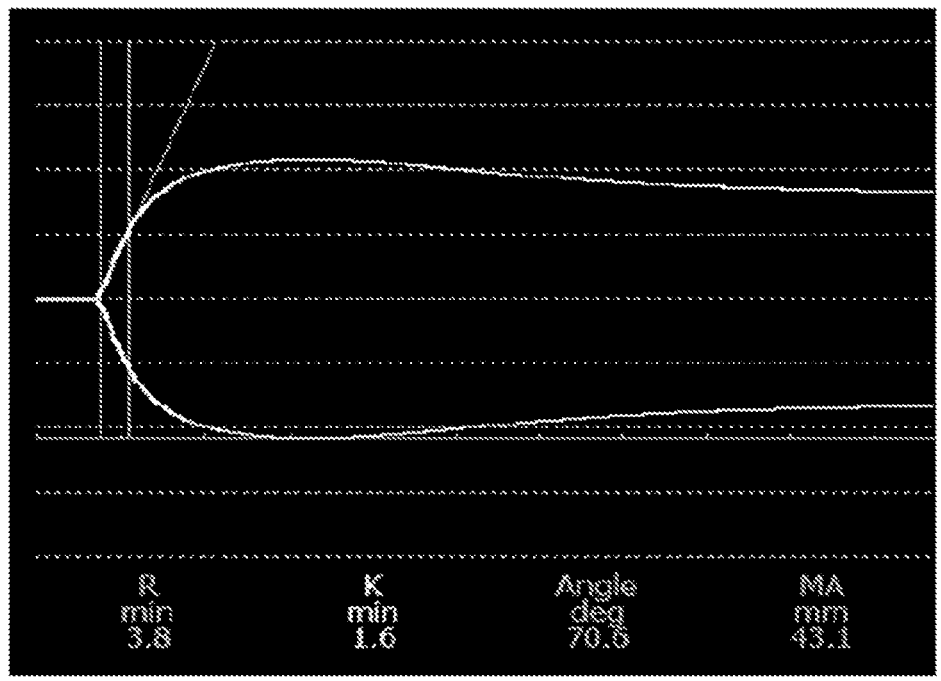

Doramapimod significantly reduced the hypercoagulable effect of LPS as seen by a shortened R time (FIG. 10). Adding the β-cyclodextrin vehicle alone did not cause this effect, proving that this was an effect of the drug itself. Thus it appears that doramapimod negates the effect of LPS on R time, prolonging it to similar values as seen with incubation alone (without LPS).

Clot lysis (% decrease in clot AUC at 30 min) was also apparently significantly increased in the presence of doramapimod; however, the cyclodextrin vehicle itself also had this effect (Table 1), and so this cannot be attributed to doramapimod. Incubation time alone (4 h at 37° C.) had no significant effect on clotting parameters.

Table 1. Effect of doramapimod on clotting parameters from thromboelastography analysis on blood samples incubated with LPS. Values represent median and range. 15 Different letters indicate statistical differences between groups (P<0.05). The following parameters are shown:

R time (reaction time, minutes): the time from start of the analysis to clot initiation K time (minutes): the time for the TEG tracing to reach a specific clot strength Ang (angle, degrees): indicator of the rate of clot formation MA (maximum amplitude, millimetres): the greatest clot strength achieved Ly30 (percent): clot lysis as determined by percent decrease in area under the curve compared to the MA at 30 minutes after MA is achieved.

|  | R (min) | K (min) | Ang (degrees) | MA (mm) | Ly30 (%) |
| --- | --- | --- | --- | --- | --- |
| Control | 5.0 (4.0-7.2)$^a$ | 1.3 (0.9-2.4) | 74.6 (63.4-78.4) | 51.7 (41.9.54.0) | 4.3 (3.2-7.1)$^a$ |
| Cyclodextrin | 5.2 (3.8-7.8)$^a$ | 1.2 (1.0-2.6) | 74.6 (58.7-76.5) | 52.5 (43.5-54.6) | 9.5 (4.8-14.2)$^b$ |
| LPS | 1.9 91.0-2.0)$^b$ | 0.9 (0.8-1.6) | 79.0 (72.3-79.7) | 50.5 (40.9-51.6) | 4.2 (3.1-9.4)$^a$ |
| LPS + DORA | 3.2 (2.2-3.8)$^a$ | 0.9 (0.8-1.6) | 78.7 (70.6-80.4) | 51.3 (43.1-54.5) | 10.7 (.09-11.5)$^b$ |

FIG. 9 shows changes in clotting parameters observed during the low-dose endotoxin infusion model. Bars represent mean±sem.

Although thromboelastography (TEG) could be used successfully to demonstrate the effects of doramapimod on clotting dysfunction when blood samples were incubated with much higher concentrations of endotoxin in the laboratory.

Example TEG traces from one horse are shown in FIG. 10, and values for each of the parameters are provided in Table 1. Incubating blood samples with 100 ng/mL LPS (endotoxin) induced a hypercoagulable state, similar to that observed in clinical cases of endotoxemia. This was shown by the reduction in the reaction (R) time, which was the time from start of the analysis to the initiation of clot formation induced by kaolin. The kaolin clotting time is equivalent to the APTT, and represents intrinsic and common coagulation pathways. The other TEG parameters were not affected by incubation with or without LPS. This is consistent with a published study looking at effects of incubation of human whole blood with LPS, in which the only indication of a hypercoagulable effect was a shortening of R time (described as clotting time [CT] in that paper).

In FIG. 10, example tracings from one horse to show the effect of LPS (endotoxin) on whole blood clotting measured by thromboelastography (TEG), and the effect of doramapimod. The R time (reaction time) was significantly shortened by LPS, and doramapimod significantly reduced this hypercoagulative state. An explanation of the parameters is provided in the legend to Table 1.

Doramapimod effectively inhibits inflammatory cell activation and cytokine production in experimental horses in response to an endotoxin challenge. Both drugs tested, rolipram and doramapimod, were shown to have anti-endotoxic effects in vitro. While both drugs reduced pro-inflammatory cytokine production, doramapimod was more potent, acting at much lower concentrations than rolipram. Also doramapimod was more efficacious in terms of the maximum inhibition of IL-1 production by activated leukocytes.

Although there were some challenges with the solubility of doramapimod, a suitable formulation was found for intravenous injection. Intravenous injection of this drug proved to be extremely safe, with no evidence of hematological or biochemical abnormalities or clinical adverse effects. In contrast, the drug rolipram has been found to cause adverse effects when given intravenously to horses and therefore investigations were focused solely on doramapimod.

As well as being very effective when added to whole blood in the lab (over a range of concentrations from very low to very high), the plasma concentrations achieved in the circulation following intravenous administration were effective at inhibiting cytokine production. It also appeared that effective plasma concentrations were maintained for at least 6 hours after injection. The dose used in this study, 0.5 mg/kg, is comparable to that tested in laboratory animals and humans and is relatively low compared to many other anti-inflammatory compounds, proving that it is very potent in its actions.

In contrast to the in vitro and ex vivo assays, the inflammatory responses in vivo may be much more complex, and so the key part of this study was using the low-dose endotoxin challenge model. This well-characterized model caused mild effects clinically but substantial cell activation and cytokine responses. Doramapimod demonstrated excellent anti-inflammatory effects in this model—clinical impressions were that the inflammatory signs of endotoxemia (increased heart rate, muscle tremors, reduced gut sounds, increased rectal temperature) were obviously blunted or almost completely abolished when the drug had been administered. This was confirmed by the fact that white blood cell activation (TNF production and cell margination out of the blood circulation) was significantly reduced.

Doramapimod significantly reduced the hypercoagulable effect of LPS in equine whole blood incubated with LPS, as seen by a significant lengthening in R time compared to incubation with LPS alone. This drug likely reduces the hypercoagulable effect of LPS through its inhibition of tissue factor expression, as documented in the human literature. P38 MAPK also plays an important role in the activation of platelets by endotoxin, although that was not specifically examined in the present study. Again, further studies are needed to evaluate the effect of doramapimod on coagulation dysfunction in clinical cases of endotoxemia.

Example 3

Reduction in Clinical Severity Using Doramapimod

Examples 1 and 2 show that the drug, doramapimod, reduces inflammatory cytokine production by equine leukocytes in whole blood assays. Furthermore, this drug has also been shown to reduce clinical signs of endotoxemia in vivo, in a low dose endotoxin challenge study in experimental horses. As part of these studies, the drug in its developed formulation has been found to be safe for intravenous administration. The next stage in the development of this drug as a treatment for endotoxemia in horses is to conduct a clinical trial in naturally occurring cases.

Therefore, the aims of this Example are first to determine whether doramapimod has anti-inflammatory effects in naturally occurring clinical cases of endotoxemia and whether it reduces disease severity. Secondly, this study will provide information necessary for the design of larger clinical trials. Six treated and five control animals were enrolled in this initial pilot trial.

Horses were selected with naturally occurring endotoxemia due to inflammatory intestinal disease of a medical (non-surgical) nature, such as colitis or anterior enteritis.

All cases were treated with the standard routine therapy, including the non-steroidal anti-inflammatory drug (NSAID), flunixin meglumine.

The drug treatment group additionally received doramapimod by IV injection at a dose of 0.5 mg/kg. Up to 3 doses were given, 24 h apart, i.e. one dose every 24 hours for up to 72 hours. The first dose was given after examination and enrolment on the day of presentation if presenting before 5 pm. If presenting in the late evening then that counted as Day 0.

The placebo control group received injections of the vehicle control (cyclodextrin in saline).

Figure 18:
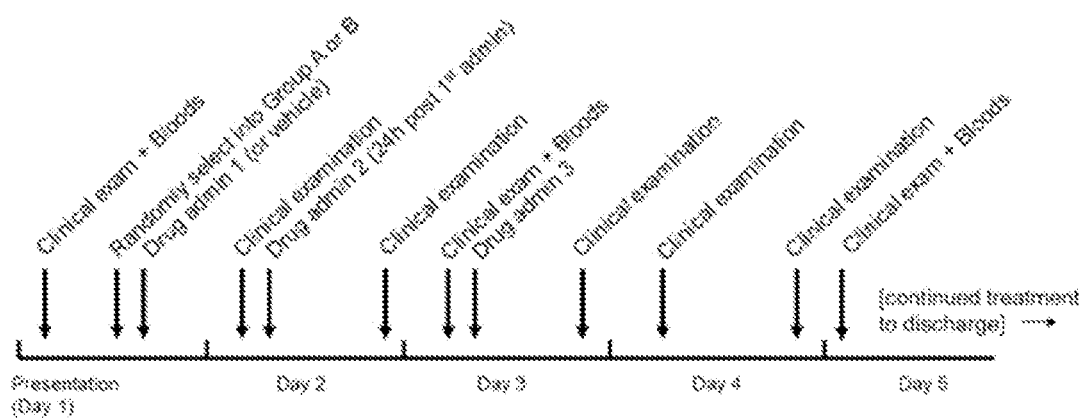
FIG. 18 illustrates the case timeline for Example 3.

The timeline is provided in FIG. 18.

The following clinical signs were recorded twice daily (am and pm):
heart rate, respiratory rate;
rectal temperature;
intestinal sounds;
mucous membrane colour and capillary refill time;
sepsis score (Breuer and Schusser (2012) *Pferdeheilkunde* 28:421-428; clinical assessment combined with leukocyte count; once daily assessment);
any other necessary investigations Blood samples were taken on the day of presentation, then days 3 and 5. The parameters measured included basic biochemistry, haematology (haematocrit, leukocytes, differential counts, platelets) and plasma fibrinogen.

In addition to the above parameters, sepsis scores were calculated, using the method established by Breuer and Schusser (2012). Time to discharge, Mortality rate and cost of treatment were also recorded.

Blinding and Randomization

Clinicians were blinding to treatment versus vehicle. The drug or vehicle were decided in random order by simple lottery and assigned a coded label.

Details of the individual cases are provided below:

Case I

Case number 309316; a 9 year-old Warmblood gelding (605 kg). Diagnosis: Anterior enteritis. Treatment allocation: Doramapimod (0.5 mg/kg). Outcome: Excellent recovery.

Details: This horse had a severe anterior enteritis, with intestinal ileus causing significant reflux of intestinal contents, requiring frequent stomach tubing to prevent stomach rupture. On day 1 (pre-treatment) the heart rate was 62, and white blood cell and neutrophil counts were low (1.2 and $0.3 \times 10^6$/mL, respectively). These signs had been ongoing for 3 days and the horse was not improving despite ongoing standard care. Following the first dose of doramapimod on Day 1, the intestinal ileus gradually resolved during that night and intestinal reflux ceased the next morning. The horse was much brighter, and later on Day 2 the clinicians could begin oral feeding. They commented that this was an amazing turn-around from the previous day. The horse received the second and third doses of doramapimod (Days 2 and 3; 24 h intervals), and clinical assessment on Days 3 and 5 showed continual improvement in clinical signs, with the heart rate coming down to normal (40 bpm on Day 3 and 36 bpm on Day 5) and blood leukocyte counts also normalizing (4.3 and $5.1 \times 10^6$/mL on days 3 and 5 respectively). The sepsis score decreased from 12 on Day 1 to 5 on Day 3 and 2 on Day 5. The horse went home on Day 5 eating well and fully recovered. It has continued to do well on follow up.

Case 2

Case number 309491; 1.5 year-old entire male Thoroughbred (400 kg). Diagnosis: colitis. Treatment allocation: Placebo control. Outcome: Died—euthanized due to organ failure secondary to sepsis.

Details: This horse presented with acute colitis and severe diarrhoea. Its heart rate was 60 bpm, its rectal temperature was initially just above normal (38.6° C.), and its sepsis score was 12. Its white blood cell count was elevated (total leukocytes on Day 1 was $11.0 \times 10^6$/mL), and fibrinogen was also high (4.9). Following the administration of standard therapy (including the non-steroidal drug flunixin meglumine and IV fluids), plus the vehicle placebo control, its heart rate and temperature came down on Day 3 (40 bpm and 38.0° C.) most likely due to the flunixin and fluids. However its diarrhoea continued and its white cell count continued to climb (leukocytes $18.0 \times 10^6$/mL on Day 3). By Day 5, the horse was worsening, and starting to go into organ failure; leukocyte count remained very high at $18.2 \times 10^6$/mL. It had to be euthanized on Day 7, when the organ failure progressed and it developed uroperitoneum (creatinine >300). At necropsy the horse had areas of infarction in its internal tissues (associated with poor blood perfusion and formation of clots, due to sepsis), and its bladder had ruptured.

Case 3

Case number 263380; 8 year-old arabian gelding (400 kg). Diagnosis: colitis Treatment allocation: Doramapimod (0.5 mg/kg). Outcome: Excellent and rapid recovery.

Details: This horse presented with acute colitis and severe diarrhoea. Its heart rate and rectal temperature were not elevated significantly (HR 48 bpm, temp 37.8° C.), although its sepsis score was 12. The high sepsis score was mainly due to a very low blood leukocyte count (leukocytes $2.4 \times 10^6$/mL and neutrophils $1.1 \times 10^6$/mL on Day 1), probably to the massive sequestration of white blood cells out of the circulation and into the tissues, after being activated by circulating bacterial toxins from the large intestine. The horse received one dose of doramapimod (0.5 mg/kg on Day 1), and made an excellent recovery during the day and overnight. The diarrhoea ceased and the horse rapidly became much brighter, and by Day 3 its white blood cell count had normalized (leukocytes $4.8 \times 10^6$/mL and neutrophils $2.1 \times 10^6$/mL) and its sepsis score decreased to 6. The horse was eating normally, and the owners elected to take it home on Day 3. Subsequent follow up with the owners and referring veterinarian confirmed that the horse had made a full recovery and had no further abnormal clinical signs.

Case 4

Case number 311009; a 2 year-old entire male Thoroughbred (500 kg). Diagnosis: Colitis. Treatment allocation: Doramapimod (0.5 mg/kg). Outcome: Excellent recovery Details: This horse also presented with acute colitis and severe diarrhoea. It was showing signs of bacterial endotoxemia, as evidenced by an increased heart rate (52 bpm), increased rectal temperature (39.5° C.) and a sepsis score of 9. Inspection of its white blood cell morphology showed the presence of 'band neutrophils', again consistent with excessive leukocyte activation and mobilization from the bone marrow. The horse received the three doses of doramapimod (0.5 mg/kg) as per the protocol, and again made a remarkable recovery, the sepsis score decreasing to 7 on Day 3 and down to 1 by Day 5. Band neutrophils decreased on Day 3 and were absent on Day 5, by which time leukocyte counts were normal. The horse was bright and eating, the diarrhoea subsided and the horse went home on Day 8 after a full recovery.

Case 5

Case number 311574; 5 year-old Thoroughbred gelding (450 kg). Diagnosis: Colitis Treatment allocation: Placebo control Outcome: Died—euthanized due to sepsis-associated organ failure.

Details: This horse also presented with acute colitis and severe diarrhoea. It had an increased heart rate of 80 bpm an increased rectal temperature of 39.5° C., and a sepsis score of 21. It received the vehicle placebo control on Day 1. Despite standard care including flunixin meglumine and intensive IV fluid therapy, the clinical signs progressively worsened and the following day it developed signs of colic (abdominal pain) and also multiple organ dysfunction syndrome (MODS), a sequel of sepsis. Ultimately it went into renal failure and had to be euthanized.

Case 6

Case number 313647; 8 year-old pony/stock horse gelding (350 kg). Diagnosis: Colitis Treatment allocation: Placebo control Outcome: Slow but eventual recovery.

Details: This horse also presented with acute colitis and severe diarrhoea. It had an increased heart rate of 60 bpm an increased rectal temperature of 39.9° C., but a moderate sepsis score of 10. It received the vehicle placebo control on Day 1. This case received standard care including flunixin meglumine and intensive IV fluid therapy and the rectal temperature steadily came down. Although over the following 5 days the sepsis score remained at 10, the leukocyte counts did decrease and the pony became brighter, so it was allowed home on Day 6.

Case 7

Case number 316321; 1.5 year-old Thoroughbred mare (450 kg). Diagnosis: Colitis. Treatment allocation: Doramapimod (0.5 mg/kg). Outcome: Very good recovery.

Details: This mare presented with acute colitis with diarrhoea. It had an increased heart rate peaking at 60 bpm and increased rectal temperature peaking at 39.8° C. This case received standard care including flunixin meglumine and intensive IV fluid therapy and the horse received the three doses of doramapimod (0.5 mg/kg), although it did not receive its first dose of doramapimod until Day 2 of hospitalization. There had also been some evidence of impending renal failure on Day 1 with elevated plasma creatinine, but then the horse improved rapidly by Day 3, creatinine decreasing and the sepsis score quickly dropping from 8 to 2. The rectal temperature was not markedly elevated. The leukocyte counts were initially normal but increased on Day 3 and then declined again by Day 5. The mare was very bright by Day 5 and was allowed home on Day 6.

Case 8

Case number 313647; 4 year-old Thoroughbred gelding (500 kg). Diagnosis: Colitis. Treatment allocation: Doramapimod (0.5 mg/kg). Outcome: Good recovery.

Details: This Thoroughbred gelding had peracute colitis which had not fully developed on presentation but was worsening (maximum severity on Day 3). Sepsis score was 9 on presentation and peaked at 10 on Day 3 (fibrinogen also peaked on Day 3), but then the horse started improving well. The case received standard care including flunixin meglumine and intensive IV fluid therapy and the horse received the three doses of doramapimod (0.5 mg/kg). The sepsis score was right down to 2 by Day 5, and the horse continued to improve well from there (went home on Day 8).

Case 9

Case number 316552; 14 year-old Welsh Cob gelding (500 kg). Diagnosis: Colitis. Treatment allocation: Placebo control. Outcome: Euthanized due to persistent colic and lack of improvement.

Details: This gelding presented with acute colitis with diarrhoea. It had an increased heart rate of 68 bpm and slightly increased rectal temperature of 38.5° C., and a sepsis score of 12 on Day 1. It received the vehicle placebo control on Days 1, 2 and 3. This case received standard care including flunixin meglumine and intensive IV fluid therapy. Initially the sepsis score improved partially, (score 7 on Day 3), but did not improve any further by Day 5. Although its temperature went down, heart rate remained elevated, leukocyte counts increased and creatinine remained elevated. There was no ongoing improvement beyond the initial effects of fluids and flunixin, and the gelding experienced ongoing persistent colic. Therefore the horse was euthanized on Day 5.

Case 10

Case number 319259; 12 year-old Thoroughbred mare (523 kg). Diagnosis: Anterior enteritis. Treatment allocation: Placebo control. Outcome: Survived to discharge but still quite sick.

Details: This post-partum mare (with foal at foot) presented with anterior enteritis (compare with case #1). It had intestinal stasis and required regular reflux of fluid from the stomach. Heart rate was 60 bpm, temperature spiked at 39.1.

This case received standard care including flunixin meglumine and intensive IV fluid therapy. It also received the vehicle placebo control on Day 1. The sepsis score was moderately high (8) on presentation and was still the same on Day 3. Leukocytes and neutrophils were very high on Day 1 (15.7 and 14.2 respectively) and then low on Day 3, normalising around Day 5. The mare steadily improved between Days 3 and 5, and on Day 5 when the sepsis score was 3 the owners arranged for the horse to be collected against clinical advice. However the horse was no longer refluxing and it is presumed that it continued to improve steadily.

Case 11

Case number 319518; 15 year-old Quarter Horse gelding (500 kg). Diagnosis: Colitis. Treatment allocation: Doramapimod (0.5 mg/kg). Outcome: Rapid recovery.

Details: This Quarter Horse had severe clinical signs prior to presentation, but was starting to respond to NSAIDs. The HR was still increased (52 bpm) and the sepsis score was 9 on presentation, but the temperature was not elevated. Leukocytes were low. The case received standard care including flunixin meglumine and intensive IV fluid therapy and the horse received the two doses of doramapimod (0.5 mg/kg), on Days 1 and 2. The horse improved very rapidly, sepsis score decreasing to 1 on Day 3 and 0 on Day 4. HR and WBC also normalized rapidly and the diarrhoea ceased. The horse was discharged on Day 4.

Comparison of Clinical Parameters

The key clinical parameters in the control (placebo) group and the treated group are provided in the graphs below.

Figure 11:
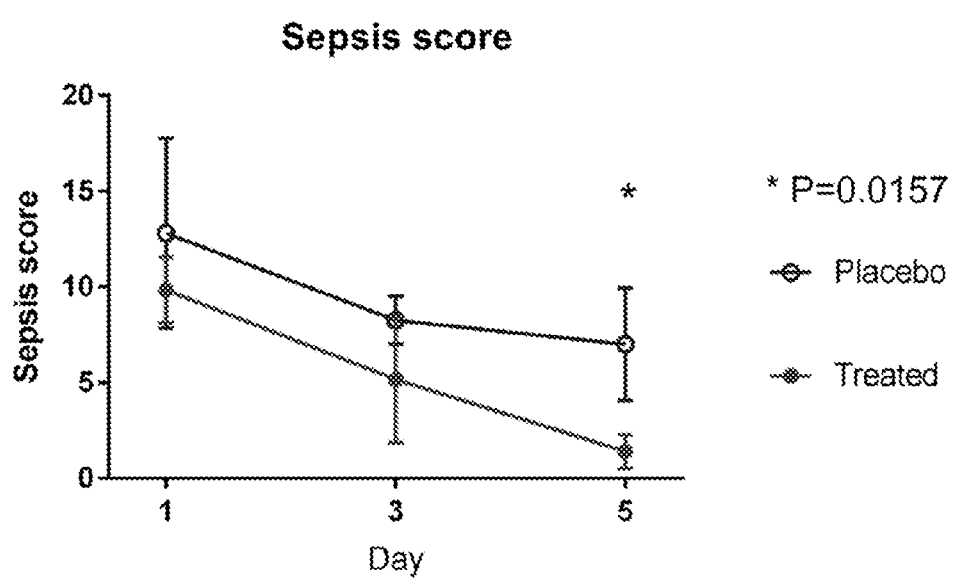
FIG. 11 is a graphical representation showing sepsis scores in clinical cases with signs of endotoxemia, with and without doramapimod treatment. Bars represent standard deviation of the mean.

The sepsis score decreased initially in both groups, probably due to the effects of flunixin and fluids, however it continued to decrease in the doramapimod treated horses, to a level which was no longer consistent with clinical disease. Sepsis scores in the placebo horses that survived to day 5 remained elevated (FIG. 11).

Figure 12:
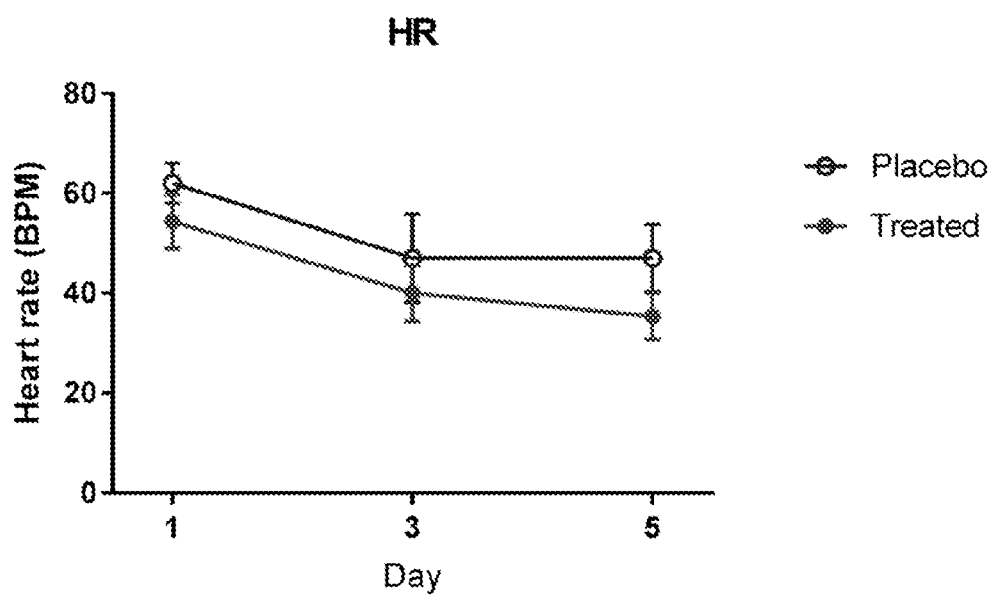
FIG. 12 is a graphical representation showing heart rate in clinical cases with signs of endotoxemia, with and without doramapimod treatment. Bars represent standard deviation of the mean.
Figure 13:
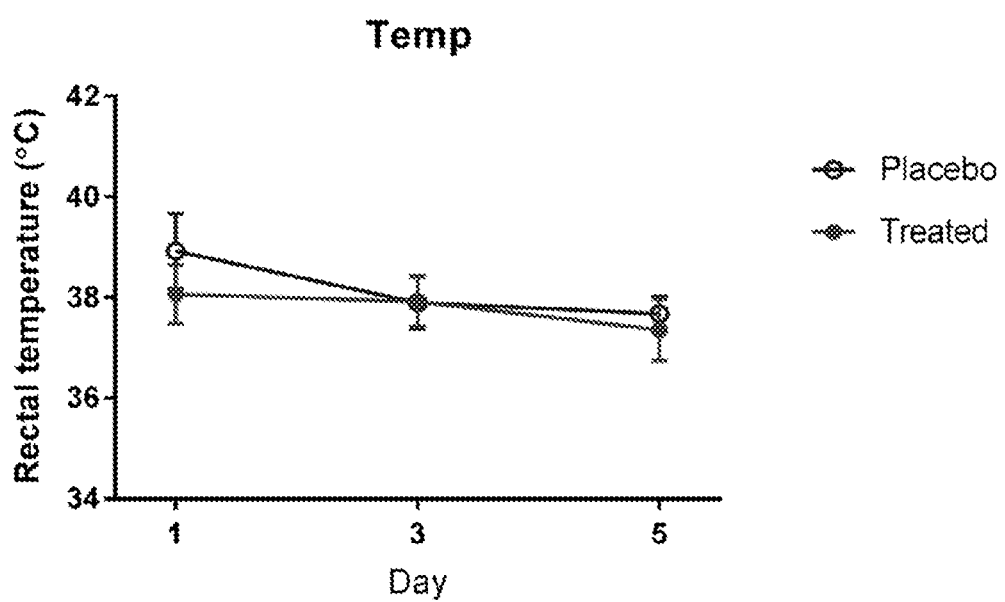
FIG. 13 is a graphical representation showing rectal temperature in clinical cases with signs of endotoxemia, with and without doramapimod treatment. Bars represent standard deviation of the mean.

There was little difference in the changes in heart rate and rectal temperature between the two groups (FIGS. 12 and 13), although these signs are improved by flunixin and fluids.

Figure 14:
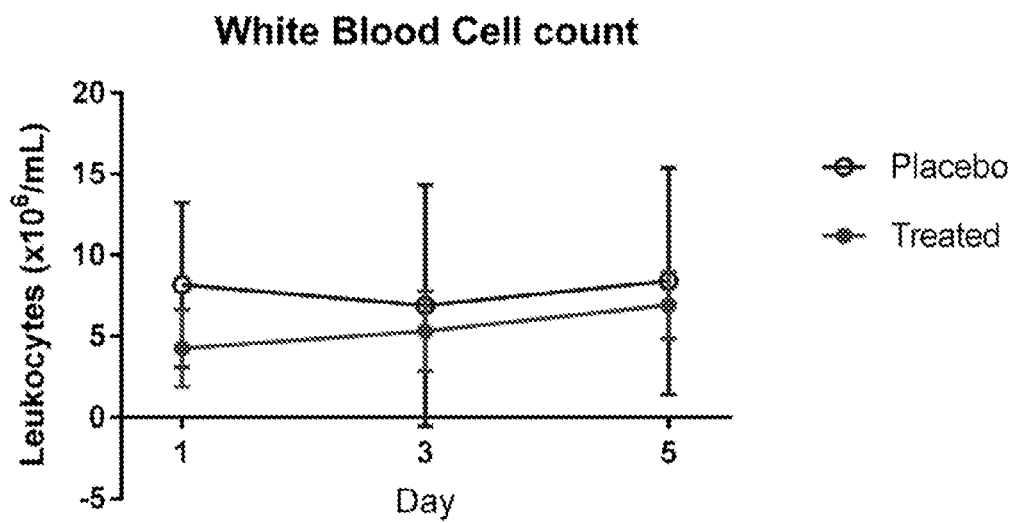
FIG. 14 is a graphical representation showing white blood cell (leukocyte) count in clinical cases with signs of endotoxemia, with and without doramapimod treatment. Bars represent standard deviation of the mean.
Figure 15:
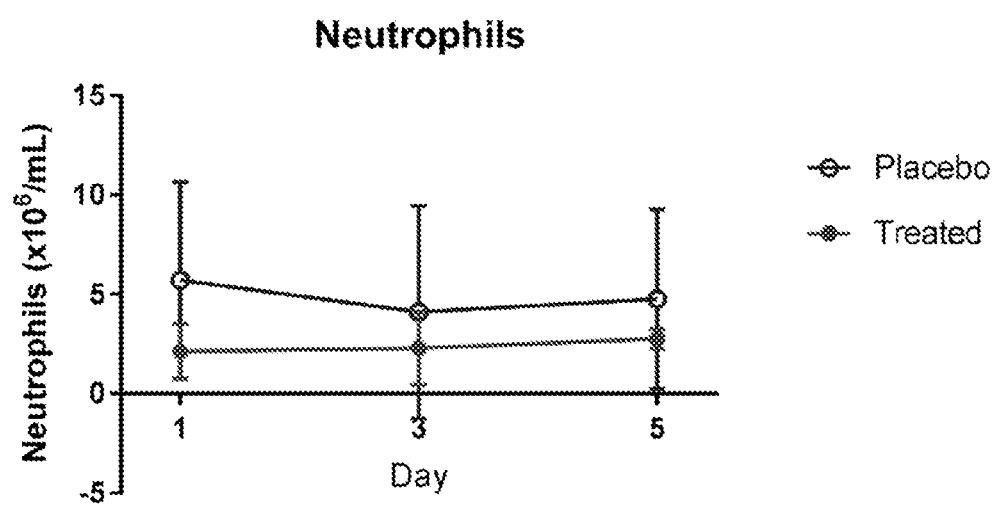
FIG. 15 is a graphical representation showing blood neutrophil count in clinical cases with signs of endotoxemia, with and without doramapimod treatment. Bars represent standard deviation of the mean.

Looking at the white blood cell counts, the total leukocyte count (FIG. 14) and neutrophil count (FIG. 15) either increased or decreased in the placebo treated horses that survived to Day 5 (both of which may be indicative of severe systemic inflammation), but remained in the normal range in those treated with doramapimod.

Figure 16:
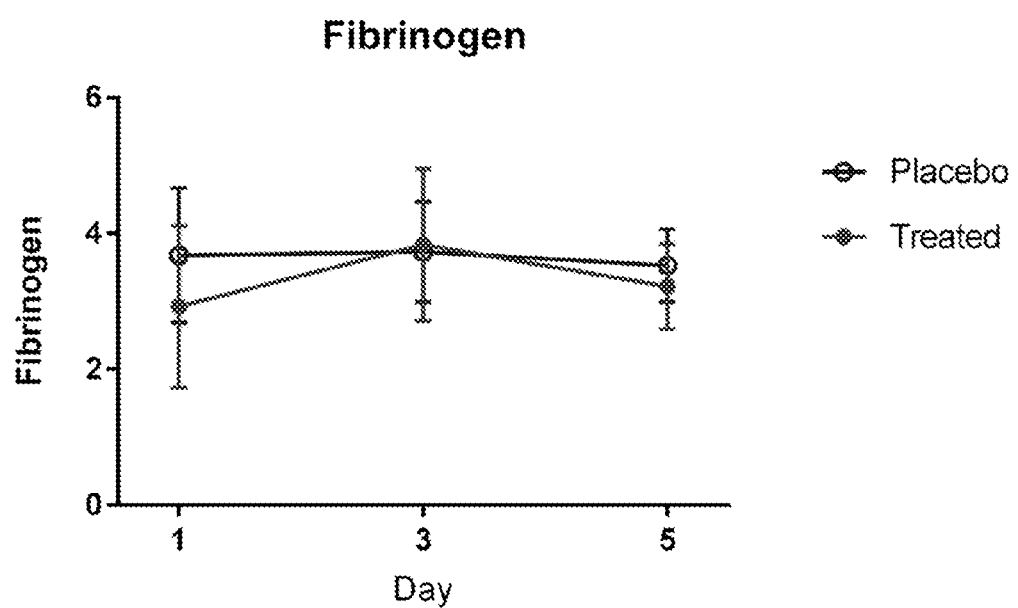
FIG. 16 is a graphical representation showing plasma fibrinogen in clinical cases with signs of endotoxemia, with and without doramapimod treatment. Bars represent standard deviation of the mean.

Fibrinogen, an acute phase inflammatory marker released from the liver in response to proinflammatory cytokines, remained elevated and even increased in the placebo treated horses but started to decrease by Day 5 in the doramapimod treated horses (FIG. 16). This acute phase protein takes several days to change in response to increased or decreased systemic inflammation, so there is a significant lag phase.

Figure 17:
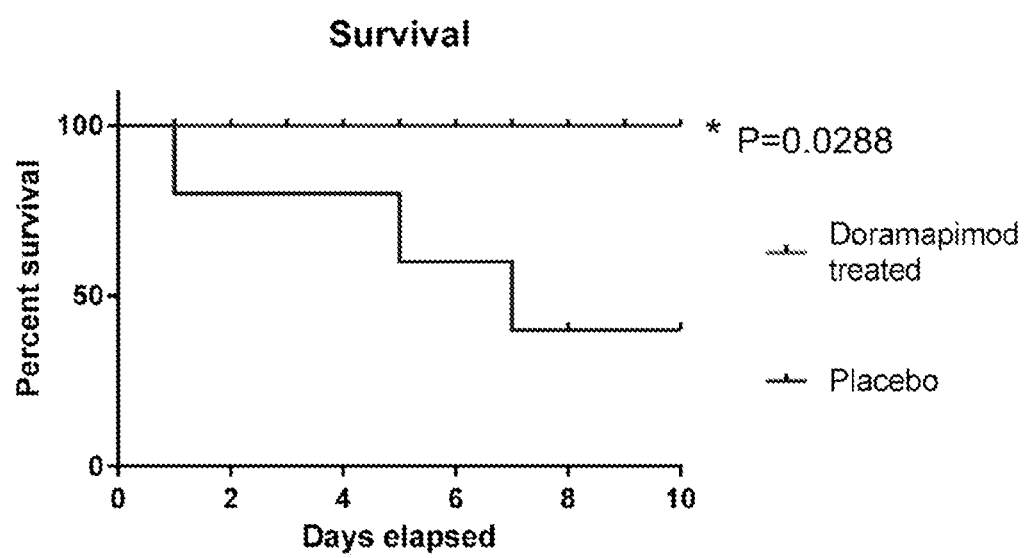
FIG. 17 is a graphical representation (Kaplan-Meier curve) showing survival of clinical cases with signs of endotoxemia, with and without doramapimod treatment.

The survival curve is shown in FIG. 17. There are insufficient cases for statistical comparison at this stage.

Importantly, the drug was well tolerated and no adverse effects were observed at any time.

The major finding from this blinded clinical trial is the rapid and remarkable recoveries of the horses treated with doramapimod, while two of the three horses that received the vehicle control continued to worsen and both had to be euthanized due to the end stages of sepsis, namely organ dysfunction and organ failure.

The increase in heart rate and rectal temperature in endotoxemia is mainly due to the effects of inflammatory prostaglandins on the vasculature and hypothalamus, respectively. Therefore these signs will be improved by the standard therapy of the NSAID flunixin meglumine, plus fluids. NSAIDs block cyclo-oxygenase and therefore prostaglandin production, but at clinical doses do not prevent leukocyte activation by bacterial endotoxin, or the production of pro-inflammatory cytokines which mediate leukocyte migration into the tissues causing organ damage and failure. Therefore, the improvement in these clinical signs with flunixin can mask the ongoing systemic inflammatory response and tissue damage.

Heart rate and rectal temperature are major components of the sepsis score, and this explains the initial improvement in the sepsis score in the placebo treated horses, although the score remained high as tissue damage and organ failure developed.

Inflammatory cytokines in the blood tend to be transient, and routine assays are not available. The most commonly used inflammatory marker in equine medicine is fibrinogen, an acute phase protein released from the liver in response to proinflammatory cytokines. In this study it persistently increased in the placebo treated horses but started reducing by Day 5 in the doramapimod treated horses.

White blood cell counts may increase or decrease with sepsis. Typically there is increased production and mobilization of leukocytes into the blood stream, particularly neutrophils, although with the initial systemic activation of leukocytes and vascular endothelial cells the leukocyte count may drop as the cells marginate and move into the tissues.

While the leukocyte and neutrophil counts either increased or decreased in the placebo treated horses that survived to Day 5 (both of which may be indicative of severe systemic inflammation), they remained in the normal range in those treated with doramapimod. One treated horse had a low leukocyte count which normalized following doramapimod therapy.

In conclusion, doramapimod is well tolerated and no adverse effects were observed, consistent with the previous tolerability studies in the in vivo experimental endotoxemia model. In all of the clinical cases treated to date, the drug produced a remarkable beneficial effect, to an extent that surprised the attending clinicians. In two of the cases that received the vehicle without the drug, the other standard therapies were not sufficient to prevent the worsening of clinical signs, ongoing leukocyte activation and eventual organ failure.

Those skilled in the art will appreciate that the disclosure described herein is susceptible to variations and modifications other than those specifically described. It is to be understood that the disclosure contemplates all such variations and modifications. The disclosure also enables all of the steps, features, compositions and compounds referred to or indicated in this specification, individually or collectively, and any and all combinations of any two or more of the steps or features or compositions or compounds.

All patents, applications, publications, test methods, literature, and other materials cited herein are hereby incorporated by reference in their entirety as if physically present in this specification.

BIBLIOGRAPHY

Ansel and Popovish (1990) *Pharmaceutical Dosage Forms and Drug Delivery Systems*, 5th ed., Lea and Febiger
Balis et al. (1979) *Lab Invest* 40:55-65
Balk (2014) *Virulence* 5(1):20-26
Breuer and Schusser (2012) *Pferdeheilkunde* 28:421-423
Fehr et al. (2015) *Cell Physiol Biochem* 36:2237-2249

McCue (1985) *Arch Intern Med* 145:1212-1216
Moore (1988) *Vet Clin North Am Equin Pract* 4:105-113
Moore and Vandenplas (2014) *Vet Clin Equine* 30:337-351
Morris (1991) *J Vet Int Med* 5:167-181
Remington's Pharmaceutical Sciences (1990) 18th Ed., Mack Publishing, Company
van Deventer et al. (1988) *Gastroenterology* 94:825-831
Woolcock (1985) *Aust Vet J* 62:177-181
Xing (2015) *MAP Kinase* 4(5508):24-30
Ziegler (1988) In Wyngaarden and Smith, eds. *Cecil Textbook of Medicine* 18$^{th}$ ed. Philadelphia: WB Saunders 1658-1661

The invention claimed is:

1. A method of treating endotoxemia, symptoms of endotoxemia, a condition leading to endotoxemia, or a complication arising from endotoxemia in an equine animal, said method comprising administering to the equine animal an amount of a p38 mitogen-activated protein kinase (p38 MAPK) inhibitor for a time and under conditions sufficient to treat the endotoxemia, symptoms of the endotoxemia, condition leading to endotoxemia, or the complication arising from endotoxemia in said equine animal; wherein the p38 MAPK inhibitor comprises doramapimod (1-[5-tert-butyl-2-p-tolyl-2H-pyrazol-3-yl]-3-[4-(2-morpholin-4-yl-ethoxy)naphthalen-1-yl]-urea) or a pharmaceutically acceptable salt, prodrug or solvate thereof.

2. The method of claim 1, wherein the animal exhibits a condition or symptoms of condition selected from the group consisting of laminitis, postoperative ileus, acute abdominal disease, colitis, peritonitis, pleuropneumonia, metritis, effects of exertion, septicaemia, recurrent airway obstruction, inflammatory airway disease and exercise-induced pulmonary hemorrhage which lead to endotoxemia.

3. The method of claim 1, wherein the symptoms of endotoxemia are selected from the group consisting of tachycardia, tachypnea, fever, discolored mucus membrane, prolonged capillary refill time, dehydration and decreased gastrointestinal borborygmi.

4. The method of claim 1, wherein the p38 MAPK inhibitor is administered via parenteral administration.

5. The method of claim 4, wherein the parenteral administration is via intravenous injection.

6. The method of claim 1, wherein the p38 MAPK inhibitor is administered in a parenteral formulation comprising cyclodextrin.

7. A method of treating laminitis, symptoms of laminitis, a condition leading to laminitis, or a complication arising from laminitis in an equine animal, said method comprising administering to the equine animal an amount of a p38 mitogen-activated protein kinase (p38 MAPK) inhibitor for a time and under conditions sufficient to treat the laminitis, symptoms of laminitis, condition leading to laminitis, or the complication arising from laminitis in said equine animal, wherein the p38 MAPK inhibitor comprises doramapimod (1-[5-tert-butyl-2-p-tolyl-2H-pyrazol-3-yl]-3-[4-(2-morpholin-4-yl-ethoxy)naphthalen-1-yl]-urea) or a pharmaceutically acceptable salt, prodrug or solvate thereof.

8. A method of treating postoperative ileus, symptoms of postoperative ileus, a condition leading to postoperative ileus or a complication arising from postoperative ileus in an equine animal, said method comprising administering to the equine animal an amount of a p38 mitogen-activated protein kinase (p38 MAPK) inhibitor for a time and under conditions sufficient to ameliorate treat the postoperative ileus, symptoms of postoperative ileus, condition leading to postoperative ileus, or the complication arising from postoperative ileus in said equine animal, wherein the p38 MAPK inhibitor comprises doramapimod (1-[5-tert-butyl-2-p-tolyl-2H-pyrazol-3-yl]-3-[4-(2-morpholin-4-yl-ethoxy)naphthalen-1-yl]-urea) or a pharmaceutically acceptable salt, prodrug or solvate thereof.

9. The method of claim 7, wherein the p38 MAPK inhibitor is administered via parenteral administration.

10. The method of claim 7, wherein the p38 MAPK inhibitor is administered in a parenteral formulation comprising cyclodextrin.

11. The method of claim 9, wherein the parenteral administration is via intravenous injection.

12. The method of claim 4, wherein the parenteral administration is via intravenous injection for a period of less than 5 days.

13. The method of claim 9, wherein the parenteral administration is via intravenous injection for a period of less than 5 days.

14. The method of claim 8, wherein the p38 MAPK inhibitor is administered via parenteral administration.

15. The method of claim 8, wherein the p38 MAPK inhibitor is administered in a parenteral formulation comprising cyclodextrin.

16. The method of claim 14, wherein the parenteral administration is via intravenous injection.

17. The method of claim 14, wherein the parenteral administration is via intravenous injection for a period of less than 5 days.

* * * * *